US012060323B2

(12) United States Patent
Miyake et al.

(10) Patent No.: US 12,060,323 B2
(45) Date of Patent: Aug. 13, 2024

(54) 6-HYDROXY-3-HEXENYL ALKOXYMETHYL ETHER COMPOUND AND A PROCESS FOR PREPARING A 3,13-OCTADECADIEN-1-OL COMPOUND FROM THE SAME

(71) Applicant: Shin-Etsu Chemical Co., Ltd., Tokyo (JP)

(72) Inventors: Yuki Miyake, Joetsu (JP); Takeshi Kinsho, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 18/303,008

(22) Filed: Apr. 19, 2023

(65) Prior Publication Data

US 2023/0312454 A1 Oct. 5, 2023

Related U.S. Application Data

(62) Division of application No. 17/489,908, filed on Sep. 30, 2021, now Pat. No. 11,661,394.

(30) Foreign Application Priority Data

Oct. 2, 2020 (JP) ................................ 2020-167453

(51) Int. Cl.
| | |
|---|---|
| C07C 67/08 | (2006.01) |
| C07C 29/132 | (2006.01) |
| C07C 41/22 | (2006.01) |
| C07C 41/24 | (2006.01) |
| C07C 41/30 | (2006.01) |
| C07C 43/178 | (2006.01) |

(52) U.S. Cl.
CPC ............ *C07C 67/08* (2013.01); *C07C 29/132* (2013.01); *C07C 41/22* (2013.01); *C07C 41/24* (2013.01); *C07C 41/30* (2013.01); *C07C 43/178* (2013.01)

(58) Field of Classification Search
CPC ....... C07C 29/10; C07C 29/132; C07C 33/02; C07C 41/22; C07C 41/24; C07C 41/30; C07C 41/48; C07C 43/178; C07C 43/30; C07C 43/313; C07C 67/08; C07C 69/145; C07C 41/26; C07C 43/315; C07C 41/20; C07C 29/128; C07C 33/035; C07C 69/14
See application file for complete search history.

(56) References Cited

U.S. PATENT DOCUMENTS

| | | | | |
|---|---|---|---|---|
| 2013/0245313 A1* | 9/2013 | Miyake | ................. | C07C 29/128 560/261 |
| 2022/0106247 A1 | 4/2022 | Miyake et al. | | |
| 2022/0106253 A1 | 4/2022 | Miyake et al. | | |

FOREIGN PATENT DOCUMENTS

| | | |
|---|---|---|
| KR | 20180056877 A | 5/2018 |
| WO | 2018150379 A2 | 8/2018 |

OTHER PUBLICATIONS

"Nickel Boride" Encyclopedia of Reagents for Organic Synthesis, vol. 6, pp. 3694-3699 (2001).
Abstracts of the 1st Latin American Meeting of Chemical Ecology, Colonia del Sacramento, Uruguay (200 pages) (Oct. 17-20, 2010).
Gardette et al. "General Methodology for the synthesis of conjugated dienic insect sex pheromones" Tetrahedron, 40(14):2741-2750 (1984).
Legrand et al. "Synthesis and Field Tests of Sex Pheromone Components of the Leafroller *Argyrotaenia sphaleropa*" Z Naturforsch C J Biosci., 59(9-10):708-712 (2004).
Mozuraitis et al. "Identification of Minor Sex Pheromone Components of the Poplar Clearwing Moth *Paranthrene tabaniformis* (Lepidoptera, Sesiidae)" Zeitschrift für Naturforschung C, 62:138-142 (2007).
Naka et al. "Synthesis and Characterization of 3,13- and 2,13-Octadecadienyl Compounds for Identification of the Sex Pheromone Secreted by a Clearwing Moth, *Nokona pernix*" Bioscience, Biotechnology, and Biochemistry, 70(2):508-516 (2006).
Nielsen et al. "Response of Male Clearwing Moths to Caged Virgin Females, Female Extracts, and Synthetic Sex Attractants" Environmental Entomology, 4(3):451-454 (1975).
Ochiai et al. "Stereoselective synthesis of E- and Z-9,11-Dodecadien-1-yl acetates: The major sex pheromones of the red bollworm moth" Chemical and Pharmaceutical Bulletin, 31(5):1641-1645 (1983).
Sasaerila et al. "Identification of Sex Pheromone Components of Nettle Caterpillar, *Setothosea asigna*" Journal of Chemical Ecology, 23(9):2187-2196 (1997).
Sasaerila et al. "Sex Pheromone Components of Nettle Caterpillar, *Setora nitens*" Journal of Chemical Ecology, 26(8):1983-1990 (2000).
Siderhurst et al. "n-Butyl (E)-7,9-decadienoate: sex pheromone component of the nettle caterpillar, *Darna pallivitta*" Entomologia Experimentalis et Applicata, 125:63-69 (2007).
Vickers et al. "Sex pheromone components of the clearwing borer, *Carmenta chrysophanes* (Meyrick) (Lepidoptera:Sesiidae): Provisional identification and field tests" Australian Journal of Entomology, 40:69-73 (2001).
Wakamura et al. "Sex pheromone of the blue-striped nettle grub moth *Parasa lepida* (Cramer) (Lepidoptera:Limacodidae): Identification and field attraction" Applied Entomology and Zoology, 42(3):347-352 (2007).
Yadav et al. "Short and Stereoselective Syntheses of Pheromone Components of Aproaerema Modicella" Synthetic Communications, 25(24):4035-4043 (1995).
Jameson, Victoria J.A, et al., "Synthesis of triphenylphosphonium vitamin E derivatives as mitochondria-targeted antioxidants", Tetrahedron 71:8444-8453 (Sep. 5, 2015).

* cited by examiner

*Primary Examiner* — Jafar F Parsa
*Assistant Examiner* — Blaine G Doletski
(74) *Attorney, Agent, or Firm* — Myers Bigel, P.A.

(57) ABSTRACT

The present invention relates to a 6-hydroxy-3-hexenyl alkoxymethyl ether compound of the following general formula (1): $HOCH_2CH_2CH=CHCH_2CH_2OCH_2OCH_2R^1$ (1), $R^1$ representing a hydrogen atom, an n-alkyl group having 1 to 9 carbon atoms, or a phenyl group; and also relates to a process for preparing a 3,13-octadecadien-1-ol compound of the following formula (6): $CH_3(CH_2)_3CH=CH(CH_2)_8CH=CHCH_2CH_2OH$ (6) from the 6-hydroxy-3-hexenyl alkoxymethyl ether compound (1).

1 Claim, No Drawings

6-HYDROXY-3-HEXENYL ALKOXYMETHYL ETHER COMPOUND AND A PROCESS FOR PREPARING A 3,13-OCTADECADIEN-1-OL COMPOUND FROM THE SAME

TECHNICAL FIELD

The present invention relates to a 6-hydroxy-3-hexenyl alkoxymethyl ether compound and a process for preparing a 3,13-octadecadien-1-ol compound from the same.

BACKGROUND ART

Clearwing borer (*Carmenta chrysophanes*) is known as a pest against persimmon in Australia. It is reported that a proper timing for traditional insecticide application effective for the pest is unknown and that the insecticide itself is less effective for the pest (Non-Patent Literature 1 listed below). Poplar clearwing moth (*Paranthrene tabaniformis*) is one of the most serious pests against poplar in the Northern Hemisphere, and is known to be difficult to control. One of sex pheromones of *Paranthrene tabaniformis* is a 3,13-octadecadien-1-ol compound (Non-Patent Literature 2 listed below). Accordingly, biological control methods have been attracting attention, and utilization of sex pheromone substances is expected as one of them.

The 3,13-octadecadien-1-ol compound was extracted from adult females of *Carmenta foraseminis* which has recently seriously damaged cacao in South America including Peru. This compound is thought to be a sex pheromone candidate, and its utilization is expected (Non-Patent Literature 3 listed below).

A process for preparing a 3,13-octadecadien-1-ol compound is described in Patent Literature 1 listed below. In the process, a starting material, 1-hexyne, is subjected to a coupling reaction with 1,8-dibromohexane in the presence of n-butyllithium in tetrahydrofuran and hexamethylphosphoric triamide to synthesize 14-bromo-5-tetradecyne. Next, the 14-bromo-5-tetradecyne thus obtained is subjected to a hydrogenation using 5% palladium-barium sulfate as a catalyst and quinoline as a catalyst poison so that the carbon-carbon triple bond is reduced to a carbon-carbon double bond to synthesize (5Z)-14-bromo-5-tetradecene. Subsequently, 3-butyn-1-ol and lithium are reacted with each other in the presence of ammonia and then subjected to a coupling reaction with the (5Z)-14-bromo-5-tetradecene to synthesize (13Z)-octadecen-3-yn-1-ol. Then, the carbon-carbon triple bond of the (13Z)-octadecen-3-yn-1-ol is reduced to a carbon-carbon double bond.

Another process for preparing a 3,13-octadecadien-1-ol compound is described in Non-Patent Literature 5 listed below. In the process, a starting material, 1,9-nonanediol, is subjected to half bromination of one of its hydroxyl groups with hydrogen bromide and the protection of the other hydroxyl group with 2,3-dihydropyran to synthesize 2-[(9-bromononyl)oxy]tetrahydro-2H-pyran. Next, the 2-[(9-bromononyl)oxy]tetrahydro-2H-pyran thus obtained is reacted with 1-hexynyllithium in tetrahydrofuran and hexamethylphosphoric triamide and then subjected to Birch reduction with metallic lithium. Then, the 2-tetrahydropyranyl group is removed to obtain 10-pentadecen-1-ol. Subsequently, the hydroxyl group of the 10-pentadecen-1-ol thus obtained is iodinated with iodine in the presence of imidazole as a base, and triphenylphosphine in a mixed solvent of diethyl ether and acetonitrile to synthesize 15-iodo-5-pentadecene. Next, 3-butynyl tetrahydropyranyl ether is reacted with n-butyllithium in tetrahydrofuran and hexamethylphosphoric triamide and then subjected to a coupling reaction with the 15-iodo-5-pentadecene to synthesize (13E)-13-octadecen-3-yl tetrahydropyranyl ether. Subsequently, (13E)-13-octadecen-3-yl tetrahydropyranyl ether thus obtained is subjected to a hydrogenation using 5% palladium-barium sulfate as a catalyst and quinoline as a catalyst poison so that its carbon-carbon triple bond at the position 3 is reduced to a carbon-carbon double bond. Finally, the 2-tetrahydropyranyl group is removed.

A 3,13-octadecadienyl acetate compound is also known as a sex pheromone of many clearwings such as Peachtree borer (*Synanthedon exitiosa*) (Non-Patent Literature 4 listed below). The 3,13-octadecadienyl acetate compound is reportedly prepared by acetylating a 3,13-octadecadien-1-ol compound (Non-Patent Literature 5 listed below).

LIST OF THE LITERATURES

Patent Literature

[Patent Literature 1] KR-A-180056877

Non-Patent Literatures

[Non-Patent Literature 1] Richard A Vickers et al., 2001, Australian Journal of Entomology, 40: 69-73.
[Non-Patent Literature 2] Raimondas Mozuraitis et al., 2007, Z. Naturforsch., 62C: 138-142.
[Non-Patent Literature 3] Abstracts of the 1st Latin American Meeting of Chemical Ecology Colonia del Sacramento, Uruguay Oct. 17-20, 2010
[Non-Patent Literature 4] D. G. Nielsen et al., 1975, Environmental entomology, 3 (1): 451-454.
[Non-Patent Literature 5] T. Ando et al., 2006, Biosci. Biotechnol. Biochem., 70 (2): 508-516.
[Non-Patent Literature 6] Thomas J. Caggiano et al. Encyclopedia of Reagents for Organic Synthesis: 3694-3699.

Problems to be Solved by the Invention

In the preparation processes described in Patent Literature 1 and Non-Patent Literature 5, hexamethylphosphoric triamide is used as a solvent in a large amount. This solvent is carcinogenic, which makes the processes difficult for industrial application.

Expensive palladium catalyst is used in the hydrogenation, which make the processes economically less advantageous. Quinoline used as a catalyst poison in the processes is recently considered to adversely affect the human body, and is difficult to be used industrially. Ammonia used in the coupling reaction and Birch reduction causes a serious symptom upon inhalation even at a low concentration and is regulated by the Offensive Odor Control Act and the High Pressure Gas Safety Act. This requires a special equipment and makes the processes unsuitable for industrial production. The processes use metallic lithium, which ignites easily in contact with water, which is unfavorable for industrial application. The processes comprise many steps. Further, a double bond is formed at position 3 by reduction in the later stage, which causes a risk that the double bond, at position 13, formed by reduction in the former stage is also hydrogenated to by-produce 3-octadecen-1-ol so as to decrease purity.

SUMMARY OF THE INVENTION

The present invention has been made in these circumstances, and aims to provide a process for efficiently preparing 3,13-octadecadien-1-ol compounds in a high purity.

As a result of the intensive researches to overcome the aforesaid problems of the prior art, the present inventors have found that a 6-hydroxy-3-hexenyl alkoxymethyl ether compound is a useful starting material for the preparation of a 3,13-octadecadien-1-ol compound. The present inventors have also found that use of the 6-hydroxy-3-hexenyl alkoxymethyl ether compound makes it possible to efficiently prepare the 3,13-octadecadien-1-ol compound in shorter steps and in a high purity, while controlling stereoisomerisim at the position 3 and position 13, and thus have completed the present invention.

According to one aspect of the present invention, there is provided a process for preparing a 3,13-octadecadien-1-ol compound of the following formula (6):

$$CH_3(CH_2)_3CH=CH(CH_2)_8CH=CHCH_2CH_2OH \quad (6),$$

the process comprising:
halogenating a 6-hydroxy-3-hexenyl alkoxymethyl ether compound of the following general formula (1):

$$HOCH_2CH_2CH=CHCH_2CH_2OCH_2OCH_2R^1 \quad (1)$$

wherein $R^1$ represents a hydrogen atom, an n-alkyl group having 1 to 9 carbon atoms, or a phenyl group to prepare a 6-halo-3-hexenyl alkoxymethyl ether compound of the following general formula (2):

$$X^1CH_2CH_2CH=CHCH_2CH_2OCH_2OCH_2R^1 \quad (2)$$

wherein $X^1$ represents a halogen atom, and $R^1$ is as defined above;
converting the 6-halo-3-hexenyl alkoxymethyl ether compound (2) into a nucleophilic reagent, 6-(alkoxymethoxy)-3-hexenyl compound of the following general formula (3):

$$MCH_2CH_2CH=CHCH_2CH_2OCH_2OCH_2R^1 \quad (3)$$

wherein M represents Li, $MgZ^2$, $CuZ^2$, or $CuLiZ^2$, wherein $Z^2$ represents a halogen atom or a 6-(alkoxymethoxy)-3-hexenyl group, and $R^1$ is as defined above;
subjecting the nucleophilic reagent, 6-(alkoxymethoxy)-3-hexenyl compound (3), to a coupling reaction with a 12-halo-5-dodecene of the following general formula (4):

$$CH_3(CH_2)_3CH=CH(CH_2)_6X^2 \quad (4)$$

wherein $X^2$ represents a halogen atom,
to prepare a 3,13-octadecadiene alkoxymethyl ether compound of the following general formula (5):

$$\begin{array}{l}CH_3(CH_2)_3CH=CH(CH_2)_8\\CH=CHCH_2CH_2OCH_2OCH_2R^1\end{array} \quad (5)$$

wherein $R^1$ is as defined above; and
dealkoxymethylating the 3,13-octadecadiene alkoxymethyl ether compound (5) to prepare the 3,13-octadecadien-1-ol compound (6).

According to another aspect of the present invention, there is provided a process for preparing a 3,13-octadecadienyl acetate compound of the following formula (7):

$$CH_3(CH_2)_3CH=CH(CH_2)_8CH=CHCH_2CH_2OAc \quad (7)$$

wherein Ac represents an acetyl group,
the process comprising:
the aforesaid process for preparing the 3,13-octadecadien-1-ol compound (6), and
acetylating the resulting 3,13-octadecadien-1-ol compound (6) to prepare the 3,13-octadecadienyl acetate compound (7).

According to another aspect of the present invention, there is provided a 6-hydroxy-3-hexenyl alkoxymethyl ether compound of the following general formula (1):

$$HOCH_2CH_2CH=CHCH_2CH_2OCH_2OCH_2R^1 \quad (1)$$

wherein $R^1$ represents a hydrogen atom, an n-alkyl group having 1 to 9 carbon atoms, or a phenyl group.

According to the present invention, it is possible to prepare the 3,13-octadecadien-1-ol compound (6) in shorter steps, in a high yield, and in a high purity.

DETAILED DESCRIPTION OF THE PREFERRED EMBODIMENTS

6-Hydroxy-3-hexenyl alkoxymethyl ether compound (1)

First, the 6-hydroxy-3-hexenyl alkoxymethyl ether compound of the following general formula (1) will be explained.

$$HOCH_2CH_2CH=CHCH_2CH_2OCH_2OCH_2R^1 \quad (1)$$

$R^1$ in the 6-hydroxy-3-hexenyl alkoxymethyl ether compound (1) represents a hydrogen atom, an n-alkyl group having 1 to 9 carbon atoms, preferably 1 to 5 carbon atoms, more preferably 1 to 2 carbon atoms, or a phenyl group.

Examples of the n-alkyl group, $R^1$, include linear saturated hydrocarbon groups such as a methyl group, an ethyl group, an n-propyl group, an n-butyl group, an n-pentyl group, an n-hexyl group, an n-heptyl group, an n-octyl group, and an n-nonyl group.

Specific examples of the 6-hydroxy-3-hexenyl alkoxymethyl ether compound (1) include the following compounds:
(3E)-6-hydroxy-3-hexenyl alkoxymethyl ether compounds such as (3E)-6-hydroxy-3-hexenyl methoxymethyl ether, (3E)-6-hydroxy-3-hexenyl ethoxymethyl ether, (3E)-6-hydroxy-3-hexenyl propoxymethyl ether, (3E)-6-hydroxy-3-hexenyl butoxymethyl ether, (3E)-6-hydroxy-3-hexenyl pentyloxymethyl ether, (3E)-6-hydroxy-3-hexenyl hexyloxymethyl ether, (3E)-6-hydroxy-3-hexenyl heptyloxymethyl ether, (3E)-6-hydroxy-3-hexenyl octyloxymethyl ether, (3E)-6-hydroxy-3-hexenyl nonyloxymethyl ether, (3E)-6-hydroxy-3-hexenyl decyloxymethyl ether, and (3E)-6-hydroxy-3-hexenyl benzyloxymethyl ether; and
(3Z)-6-hydroxy-3-hexenyl alkoxymethyl ether compounds such as (3Z)-6-hydroxy-3-hexenyl methoxymethyl ether, (3Z)-6-hydroxy-3-hexenyl ethoxymethyl ether, (3Z)-6-hydroxy-3-hexenyl propoxymethyl ether, (3Z)-6-hydroxy-3-hexenyl butoxymethyl ether, (3Z)-6-hydroxy-3-hexenyl pentyloxymethyl ether, (3Z)-6-hydroxy-3-hexenyl hexyloxymethyl ether, (3Z)-6-hydroxy-3-hexenyl heptyloxymethyl ether, (3Z)-6-hydroxy-3-hexenyl octyloxymethyl ether, (3Z)-6-hydroxy-3-hexenyl nonyloxymethyl ether, (3Z)-6-hydroxy-3-hexenyl decyloxymethyl ether, and (3Z)-6-hydroxy-3-hexenyl benzyloxymethyl ether.

The 6-hydroxy-3-hexenyl alkoxymethyl ether compound (1) may be synthesized, for example, according to a chemical reaction formula comprising the following two steps.

$$R^1CH_2OCH_2OCH_2CH_2C\equiv CH \quad \xrightarrow[\text{2) Ethylene oxide}]{\text{1) Base}}$$

(9)

-continued

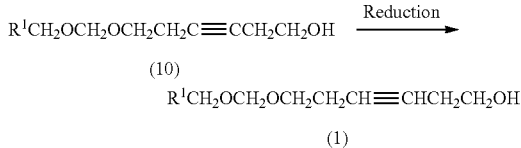

(10)

R¹CH₂OCH₂OCH₂CH₂CH═CHCH₂CH₂OH (1)

First, an alkoxymethyl 3-butynyl ether compound of the general formula (9) is reacted with a base and then with ethylene oxide to increase the number of carbon atoms to obtain a 6-hydroxy-3-hexynyl alkoxymethyl ether compound of the general formula (10) (first step). The carbon-carbon triple bond of the 6-hydroxy-3-hexynyl alkoxymethyl ether compound (10) thus obtained is reduced to obtain a 6-hydroxy-3-hexenyl alkoxymethyl ether compound (1) (second step).

The aforesaid process for preparing the 6-hydroxy-3-hexenyl alkoxymethyl ether compound (1) will be explained in more detail below.

The alkoxymethyl 3-butynyl ether compound (9) will be first explained below.

$R^1$ in the general formula (9) is as defined for the general formula (1).

Specific examples of the alkoxymethyl 3-butynyl ether compound (9) include methoxymethyl 3-butynyl ether, ethoxymethyl 3-butynyl ether, propoxymethyl 3-butynyl ether, butoxymethyl 3-butynyl ether, pentyloxymethyl 3-butynyl ether, hexyloxymethyl 3-butynyl ether, heptyloxymethyl 3-butynyl ether, octyloxymethyl 3-butynyl ether, nonyloxymethyl 3-butynyl ether, decyloxymethyl 3-butynyl ether, and benzyloxymethyl 3-butynyl ether.

Examples of the base used in the homologation reaction in which the alkoxymethyl 3-butynyl ether compound (9) is reacted with a base and then with ethylene oxide to increase the number of carbon atoms include organometallic reagents such as n-butyllithium, tert-butyllithium, methylmagnesium chloride, methylmagnesium bromide, sodium acetylide, and potassium acetylide; and metal hydride reagents, such as sodium hydride and potassium hydride. The organometallic reagents are preferred in view of the reactivity.

An amount of the base used is preferably 1.0 to 5.0 mol, more preferably 1.0 to 2.0 mol, per mol of the alkoxymethyl 3-butynyl ether compound (9) in view of the reactivity.

An amount of the ethylene oxide is preferably 1.0 to 10.0 mol, more preferably 1.0 to 3.0 mol, per mol of the alkoxymethyl 3-butynyl ether compound (9) in view of the reactivity.

A solvent may be used in the aforesaid homologation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone, N,N-dimethylformamide, N,N-dimethylacetamide, and hexamethylphosphoric triamide; and nitriles such as acetonitrile and propionitrile. Ethers such as diethyl ether, tetrahydrofuran, and 4-methyltetrahydropyran are preferred in view of the reactivity.

The solvent may be used alone or in combination thereof, if necessary. The solvent may be commercially available one.

An amount of the solvent is preferably 50 to 3,000 g, more preferably 100 to 1,200 g, per mol of the alkoxymethyl 3-butynyl ether compound (9) in view of the reactivity.

The 6-hydroxy-3-hexynyl alkoxymethyl ether compound (10) will be explained below.

$R^1$ in the general formula (10) is as defined for the general formula (1).

Specific examples of the 6-hydroxy-3-hexynyl alkoxymethyl ether compound (10) include 6-hydroxy-3-hexynyl methoxymethyl ether, 6-hydroxy-3-hexynyl ethoxymethyl ether, 6-hydroxy-3-hexynyl propoxymethyl ether, 6-hydroxy-3-hexynyl butoxymethyl ether, 6-hydroxy-3-hexynyl pentyloxymethyl ether, 6-hydroxy-3-hexynyl hexyloxymethyl ether, 6-hydroxy-3-hexynyl heptyloxymethyl ether, 6-hydroxy-3-hexynyl octyloxymethyl ether, 6-hydroxy-3-hexynyl nonyloxymethyl ether, 6-hydroxy-3-hexynyl decyloxymethyl ether, and 6-hydroxy-3-hexynyl benzyloxymethyl ether.

Examples of the reduction to synthesize the 6-hydroxy-3-hexenyl alkoxymethyl ether compound (1) include (i) a catalytic hydrogenation, (ii) a reduction using a zinc compound in an alcohol solvent, (iii) a hydroboration with a dialkylborane, followed by protonation, (iv) a reduction using potassium hydroxide and N,N-dimethylformamide (DMF) in the presence of a palladium catalyst such as palladium acetate, (v) a hydrosilylation to form vinylsilane, followed by desilylation, (vi) hydroalumination, and (vii) a Birch reduction. Preferred are the catalytic hydrogenation (i), the reduction using a zinc compound (ii), the hydroboration, followed by protonation (iii), and the hydroalumination (vi) in view of the selectivity and productivity. The catalytic hydrogenation (i) is preferred, if it is desired to form a carbon-carbon double bond in the 6-hydroxy-3-hexenyl alkoxymethyl ether compound (1) in a Z-selective manner. The hydroalumination (vi) is preferred, if it is desired to form a carbon-carbon double bond in the 6-hydroxy-3-hexenyl alkoxymethyl ether compound (1) in an E-selective manner.

(i) Catalytic Hydrogenation

The catalytic hydrogenation is carried out by supplying hydrogen gas in the presence of a metal catalyst.

Examples of the metal catalyst used in the catalytic hydrogenation include Lindlar catalyst; nickel catalysts such as P-2 nickel boride catalyst (Thomas J. Caggiano et al. Encyclopedia of Reagents for Organic Synthesis: 3694-3699) (hereinafter also referred to as "P-2 Ni catalyst"); and palladium catalysts such as palladium carbon and Pd-PEI that is palladium carbon poisoned by polyethylenimine polymer (PEI). The Lindlar catalyst and nickel catalysts are preferred, in view of the economy.

An amount of the metal catalyst varies, depending on a catalyst to be used, and is preferably 0.01 to 50 g per mol of the 6-hydroxy-3-hexynyl alkoxymethyl ether compound (10), in view of the reactivity, when the catalyst is solid like Lindlar catalyst. The P-2 Ni catalyst is preferably used in an amount of 0.001 to 0.50 mol as reduced to a nickel compound per mol of the 6-hydroxy-3-hexynyl alkoxymethyl ether compound (10). The solid catalyst may be dispersed in a solvent.

When the metal catalyst is highly active, a catalyst poison may be incorporated, if necessary.

Examples of the catalyst poison include amine compounds such as pyridine, quinoline, and ethylenediamine; phosphorus compounds such as triphenylphosphine, tritolylphosphine, and triethylphosphite; and sulfur compounds such as benzenethiol, diphenyl sulfide, dimethyl sulfide, and dimethyl sulfoxide.

An amount of the catalyst poison varies greatly, depending on a catalyst poison to be used, and is preferably 0.0001 to 10.0 g per mol of the 6-hydroxy-3-hexynyl alkoxymethyl ether compound (10) in view of the reaction rate and geometrical selectivity.

Examples of the solvent used in the catalytic hydrogenation include hydrocarbons such as hexane, heptane, benzene, toluene, xylene, and cumene; nitriles such as acetonitrile and propionitrile; esters such as methyl acetate, ethyl acetate, n-propyl acetate, and n-butyl acetate; and alcohols such as methanol, ethanol, propanol, butanol, pentanol, hexanol, 2-propanol, 2-butanol, and cyclohexanol.

The solvent may be used alone or in combination thereof, if necessary. The solvent may be commercially available one.

When Lindlar catalyst is used, the solvent is preferably a hydrocarbon such as hexane, heptane, toluene, or xylene in view of the reactivity. When a nickel catalyst is used, the solvent is preferably an alcohol such as methanol, ethanol, propanol, butanol, or 2-propanol in view of the reactivity. When a palladium catalyst such as palladium carbon is used, the solvent is preferably an ester such as methyl acetate or ethyl acetate in view of the reactivity.

An amount of the solvent used varies, depending on a catalyst and/or a solvent to be used, and is preferably 0 to 1,000 g per mol of the 6-hydroxy-3-hexynyl alkoxymethyl ether compound (10) in view of the reactivity.

A reaction temperature of the catalytic hydrogenation varies, depending on a catalyst and/or a solvent used, and is preferably 0 to 160° ° C., more preferably 20 to 100 °C, in view of the geometrical selectivity.

A reaction time of the catalytic hydrogenation is preferably 1 to 100 hours in view of the yield.

(ii) Reduction Using a Zinc Compound in an Alcohol Solvent

The reduction is carried out using a zinc compound in an alcohol solvent.

An alcohol used as the solvent has preferably 1 to 10, more preferably 1 to 5, carbon atoms. Examples of the alcohol used as the solvent include linear alcohol compounds such as methanol, ethanol, propanol, butanol, pentanol, hexanol, heptanol, octanol, nonanol, and decanol; branched alcohol compounds such as 2-propanol and 2-butanol; and cyclic alcohol compounds such as cyclohexanol. Alcohol compounds having 1 to 5 carbon atoms, such as methanol, ethanol, propanol, butanol, pentanol, and 2-propanol, are preferred in view of the reactivity.

An amount of the alcohol is preferably 46 to 1,000 g per mol of the 6-hydroxy-3-hexynyl alkoxymethyl ether compound (10) in view of the reactivity.

The zinc compound refers to metallic zinc or activated zinc as explained below.

An amount of the zinc compound is preferably 1.0 to 1,000 mol, more preferably 1.0 to 200 mol, per mol of the 6-hydroxy-3-hexynyl alkoxymethyl ether compound (10) in view of the reactivity.

The reduction may take a longer time due to the low reactivity of zinc. Then, an activator which activates zinc may be added or a zinc compound which has been activated in advance may be used.

Examples of the activator include 1,2-dibromoethane, cuprous chloride, cuprous bromide, cuprous iodide, lithium bromide, iodine, and chlorotrimethylsilane.

The activator may be used alone or in combination thereof, if necessary.

An amount of the activator is preferably 0.01 to 10.0 mol per mol of the 6-hydroxy-3-hexynyl alkoxymethyl ether compound (10) in view of the reactivity.

The activated zinc may be prepared, for example, by treating metallic zinc with an acid such as hydrochloric acid; reducing zinc chloride with metallic lithium in tetrahydrofuran; or reacting metallic zinc with 1,2-dibromoethane and lithium dibromocuprate in tetrahydrofuran.

A reaction temperature of the reduction varies, depending on a solvent to be used, and is preferably 20 to 120° C. in view of the reactivity.

A reaction time of the reduction is preferably 1 to 150 hours in view of the completion of the reaction.

(iii) Hydroboration with a Dialkylborane, Followed by Protonation

For the reduction, hydroboration is first carried out with a dialkylborane in a solvent.

The dialkylborane used in the hydroboration has preferably 4 to 18, more preferably 6 to 12, carbon atoms.

Examples of the dialkylborane include dicyclohexylborane, diisoamylborane, disiamylborane, 9-borabicyclo[3.3.1]nonane (9-BBN), diisopinocampheylborane, catecholborane, and pinacolborane. Dicyclohexylborane and diisoamylborane are preferred in view of the reactivity.

An amount of the dialkylborane is preferably 1.0 to 4.0 mol per mol of the 6-hydroxy-3-hexynyl alkoxymethyl ether compound (10) in view of the reactivity.

Examples of the solvent used in the hydroboration include ethers such as tetrahydrofuran, diethyl ether, dibutyl ether, 4-methyltetrahydropyran, cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are more preferred in view of the reactivity.

The solvent may be used alone or in combination thereof, if necessary. The solvent may be commercially available one.

An amount of the solvent is preferably 100 to 3,000 g per mol of the 6-hydroxy-3-hexynyl alkoxymethyl ether compound (10) in view of the reactivity.

A reaction temperature of the hydroboration is preferably −20° C. to 50° C. in view of the geometrical selectivity.

A reaction time of the hydroboration varies, depending on a reaction temperature and/or a reaction scale, and is preferably 1 to 100 hours in view of the reactivity.

For the reduction, protonation is carried out with an acid in a solvent after the hydroboration.

Examples of the acid used in the protonation include carboxylic acids such as acetic acid, propionic acid, butyric acid, pentanoic acid, pivalic acid, heptanoic acid, trifluoroacetic acid, chloroacetic acid, formic acid, and oxalic acid; sulfonic acids such as p-toluenesulfonic acid; and mineral acids such as sulfuric acid, hydrochloric acid, nitric acid, and phosphoric acid. Carboxylic acids such as acetic acid and propionic acid are preferred in view of the reactivity.

An amount of the acid is preferably 2.0 to 20.0 mol per mol of the 6-hydroxy-3-hexynyl alkoxymethyl ether compound (10) in view of the reactivity.

The species and an amount of the solvent are the same as those in the hydroboration, because the protonation is carried out subsequently in the hydroboration reaction system.

A reaction temperature of the protonation varies, depending on a reagent to be used, and is preferably 0° ° C. to 150° C. in view of the reaction rate. A reaction time of the protonation varies, depending on a reaction temperature and/or a reaction scale, and is preferably 1 to 70 hours in view of the reactivity.

(iv) Reduction Using Potassium Hydroxide and N,N-Dimethylformamide (DMF) in the Presence of a Palladium Catalyst Such as Palladium Acetate The reduction is carried out using potassium hydroxide and N,N-dimethylformamide (DMF) in the presence of a palladium catalyst such as palladium acetate, preferably at 100 to 180° C. for 6 to 100 hours.

(v) Hydrosilylation to Form Vinylsilane, Followed by Desilylation

The hydrosilylation is carried out using a metal catalyst, such as Wilkinson catalyst or Trost catalyst, and a trialkylsilane.

An amount of the metal catalyst is preferably 0.0001 to 4.0 mol, more preferably 0.001 to 1.0 mol, per mol of the 6-hydroxy-3-hexynyl alkoxymethyl ether compound (10) in view of the reactivity.

The hydrosilylation is preferably carried out at 5 to 100° C. for 1 to 100 hours.

The desilylation after the hydrosilylation is preferably carried out using, for example, at least one out of acid such as sulfuric acid or hydrochloric acid, hydrogen iodide, acetyl chloride, titanium tetrachloride, and iodine at 5° C. to 80° C. for 1 to 100 hours.

(vi) Hydroalumination

The hydroalumination is carried out using lithium aluminum hydride.

An amount of lithium aluminum hydride is preferably 0.25 to 4.0 mol, more preferably 0.35 to 2.0 mol, per mol of the 6-hydroxy-3-hexynyl alkoxymethyl ether compound (10) in view of the reactivity.

Examples of the solvent used in the hydroalumination include ethers such as diethyl ether, dibutyl ether, 4-methyltetrahydropyran, tetrahydrofuran (THF), cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are preferred in view of the reactivity.

The solvent may be used alone or in combination thereof, if necessary. The solvent may be commercially available one.

The hydroalumination is preferably carried out at 20 to 180° ° C. for 1 to 100 hours.

(vii) Birch Reduction

The Birch reduction is carried out using a metal in an amine or alcohol.

Examples of the metal include alkaline metals such as potassium, sodium, and lithium; and alkaline earth metals such as calcium and magnesium.

Examples of the amine include lower amines such as ammonia, methylamine, ethylamine, and propylamine.

Example of the alcohol include methanol, ethanol, and 2-methylpropanol.

The Birch reduction is preferably carried out at −78 to 20° C. for 1 to 100 hours. The geometry of the carbon-carbon double bond of the 6-hydroxy-3-hexenyl alkoxymethyl ether compound (1) may be constructed selectively in an E- or Z-configuration by choosing reduction conditions.

Preparation of 6-halo-3-hexenyl alkoxymethyl Ether Compound (2) Through Halogenation The 6-halo-3-hexenyl alkoxymethyl ether compound (2) may be prepared by halogenating the 6-hydroxy-3-hexenyl alkoxymethyl ether compound (1), as shown in the following chemical reaction formula.

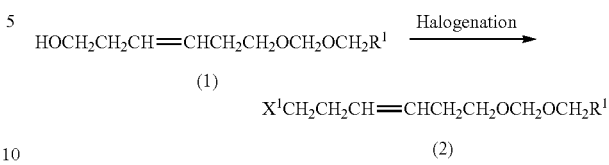

In the halogenation, one or plural species of the 6-hydroxy-3-hexenyl alkoxymethyl ether compound (1) may be used, if necessary.

For example, a mixture of a (3E)-6-hydroxy-3-hexenyl alkoxymethyl ether compound (1) and a (3Z)-6-hydroxy-3-hexenyl alkoxymethyl ether compound (1) will give a mixture of a (3E)-6-halo-3-hexenyl alkoxymethyl ether compound (2) and a (3Z)-6-halo-3-hexenyl alkoxymethyl ether compound (2).

The halogenation reaction for synthesizing 6-halo-3-hexenyl alkoxymethyl ether compound (2) may be carried out, for example, by tosylating the hydroxyl group with a p-toluenesulfonyl halide compound, followed by halogenation with a lithium halide compound or by directly halogenating the hydroxyl group with a halogenating agent.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. A methanesulfonyl halide compound, a benzenesulfonyl halide compound, or a p-toluenesulfonyl halide compound, particularly a methanesulfonyl halide compound, are more preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of the 6-hydroxy-3-hexenyl alkoxymethyl ether compound (1).

A base may be incorporated in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU); and phosphines such as tributylphosphine, triphenylphosphine, and tritolylphosphine.

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of the 6-hydroxy-3-hexenyl alkoxymethyl ether compound (1) in view of the yield and/or economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt is preferably 0 to 30.0 mol, more preferably 0 to 5.0 mol, per mol of the 6-hydroxy-3-hexenyl alkoxymethyl ether compound (1) in view of the reactivity.

Although the metal salt increases a concentration of halide ions in the reaction system to thereby enhance the reactivity, it is preferred in view of the economy and/or environmental protection not to incorporate the metal salt.

A solvent may be incorporated in the halogenation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred, in view of the reactivity. γ-Butyrolactone and acetonitrile are particularly preferred in view of the safety.

The solvent may be used alone or in combination thereof, if necessary. The solvent may be commercially available one.

An amount of the solvent used in the halogenation reaction is preferably 0 to 3,000 g, more preferably 0 to 800 g, per mol of the 6-hydroxy-3-hexenyl alkoxymethyl ether compound (1).

The solvent may occupy a part of a reactor space to reduce a space for the starting materials, resulting in a decreased productivity. Therefore, the reaction may be carried out without a solvent or with the base as the solvent.

A reaction temperature of the halogenation varies, depending on a halogenating agent to be used, and is preferably 5 to 180° C. in view of the reactivity.

A reaction time of the halogenation reaction varies, depending on a halogenating agent and/or a reaction scale, and is preferably 0.5 to 100 hours in view of the reactivity.

The 6-halo-3-hexenyl alkoxymethyl ether compound (2) will be explained below.

$X^1$ in the general formula (2) represents a halogen atom such as a fluorine atom, a chlorine atom, a bromine atom, or an iodine atom. A chlorine atom, a bromine atom, and an iodine atom, particularly a chlorine atom and a bromine atom, are preferred in view of the storage stability. $R^1$ is as defined for the general formula (1).

Specific examples of the 6-halo-3-hexenyl alkoxymethyl ether compound (2) include the following compounds:
  (3E)-6-chloro-3-hexenyl alkoxymethyl ether compounds such as (3E)-6-chloro-3-hexenyl methoxymethyl ether, (3E)-6-chloro-3-hexenyl ethoxymethyl ether, (3E)-6-chloro-3-hexenyl propoxymethyl ether, (3E)-6-chloro-3-hexenyl butoxymethyl ether, (3E)-6-chloro-3-hexenyl pentyloxymethyl ether, (3E)-6-chloro-3-hexenyl hexyloxymethyl ether, (3E)-6-chloro-3-hexenyl heptyloxymethyl ether, (3E)-6-chloro-3-hexenyl octyloxymethyl ether, (3E)-6-chloro-3-hexenyl nonyloxymethyl ether, (3E)-6-chloro-3-hexenyl decyloxymethyl ether, and (3E)-6-chloro-3-hexenyl benzyloxymethyl ether;
  (3E)-6-bromo-3-hexenyl alkoxymethyl ether compounds such as (3E)-6-bromo-3-hexenyl methoxymethyl ether, (3E)-6-bromo-3-hexenyl ethoxymethyl ether, (3E)-6-bromo-3-hexenyl propoxymethyl ether, (3E)-6-bromo-3-hexenyl butoxymethyl ether, (3E)-6-bromo-3-hexenyl pentyloxymethyl ether, (3E)-6-bromo-3-hexenyl hexyloxymethyl ether, (3E)-6-bromo-3-hexenyl heptyloxymethyl ether, (3E)-6-bromo-3-hexenyl octyloxymethyl ether, (3E)-6-bromo-3-hexenyl nonyloxymethyl ether, (3E)-6-bromo-3-hexenyl decyloxymethyl ether, and (3E)-6-bromo-3-hexenyl benzyloxymethyl ether;
  (3E)-6-iodo-3-hexenyl alkoxymethyl ether compounds such as (3E)-6-iodo-3-hexenyl methoxymethyl ether, (3E)-6-iodo-3-hexenyl ethoxymethyl ether, (3E)-6-iodo-3-hexenyl propoxymethyl ether, (3E)-6-iodo-3-hexenyl butoxymethyl ether, (3E)-6-iodo-3-hexenyl pentyloxymethyl ether, (3E)-6-iodo-3-hexenyl hexyloxymethyl ether, (3E)-6-iodo-3-hexenyl heptyloxymethyl ether, (3E)-6-iodo-3-hexenyl octyloxymethyl ether, (3E)-6-iodo-3-hexenyl nonyloxymethyl ether, (3E)-6-iodo-3-hexenyl decyloxymethyl ether, and (3E)-6-iodo-3-hexenyl benzyloxymethyl ether;
  (3Z)-6-chloro-3-hexenyl alkoxymethyl ether compounds such as (3Z)-6-chloro-3-hexenyl methoxymethyl ether, (3Z)-6-chloro-3-hexenyl ethoxymethyl ether, (3Z)-6-chloro-3-hexenyl propoxymethyl ether, (3Z)-6-chloro-3-hexenyl butoxymethyl ether, (3Z)-6-chloro-3-hexenyl pentyloxymethyl ether, (3Z)-6-chloro-3-hexenyl hexyloxymethyl ether, (3Z)-6-chloro-3-hexenyl heptyloxymethyl ether, (3Z)-6-chloro-3-hexenyl octyloxymethyl ether, (3Z)-6-chloro-3-hexenyl nonyloxymethyl ether, (3Z)-6-chloro-3-hexenyl decyloxymethyl ether, and (3Z)-6-chloro-3-hexenyl benzyloxymethyl ether;
  (3Z)-6-bromo-3-hexenyl alkoxymethyl ether compounds such as (3Z)-6-bromo-3-hexenyl methoxymethyl ether, (3Z)-6-bromo-3-hexenyl ethoxymethyl ether, (3Z)-6-bromo-3-hexenyl propoxymethyl ether, (3Z)-6-bromo-3-hexenyl butoxymethyl ether, (3Z)-6-bromo-3-hexenyl pentyloxymethyl ether, (3Z)-6-bromo-3-hexenyl hexyloxymethyl ether, (3Z)-6-bromo-3-hexenyl heptyloxymethyl ether, (3Z)-6-bromo-3-hexenyl octyloxymethyl ether, (3Z)-6-bromo-3-hexenyl nonyloxymethyl ether, (3Z)-6-bromo-3-hexenyl decyloxymethyl ether, and (3Z)-6-bromo-3-hexenyl benzyloxymethyl ether; and (3Z)-6-iodo-3-hexenyl alkoxymethyl ether compounds such as (3Z)-6-iodo-3-hexenyl methoxymethyl ether, (3Z)-6-iodo-3-hexenyl ethoxymethyl ether, (3Z)-6-iodo-3-hexenyl propoxymethyl ether, (3Z)-6-iodo-3-hexenyl butoxymethyl ether, (3Z)-6-iodo-3-hexenyl pentyloxymethyl ether, (3Z)-6-iodo-3-hexenyl hexyloxymethyl ether, (3Z)-6-iodo-3-hexenyl heptyloxymethyl ether, (3Z)-6-iodo-3-hexenyl octyloxymethyl ether, (3Z)-6-iodo-3-hexenyl nonyloxymethyl ether, (3Z)-6-iodo-3-hexenyl decyloxymethyl ether, and (3Z)-6-iodo-3-hexenyl benzyloxymethyl ether.

As shown in the following chemical reaction formula, the 6-halo-3-hexenyl alkoxymethyl ether compound (2) is converted into a nucleophilic reagent, 6-(alkoxymethoxy)-3-hexenyl compound (3), which is then subjected to a coupling reaction with a 12-halo-5-dodecene compound (4) to obtain the 3,13-octadecadiene alkoxymethyl ether compound (5).

The solvent may be used alone or in combination thereof, if necessary. The solvent may be commercially available one.

An amount of the solvent used is preferably 50 to 5,000 g, more preferably 100 g to 3,000 g, per mol of the 6-halo-3-hexenyl alkoxymethyl ether compound (2) in view of the reactivity.

A reaction temperature of the conversion with magnesium varies, depending on a solvent to be used, and is preferably 0 to 120° C. in view of the reactivity.

A reaction time of the conversion with magnesium varies, depending on a solvent and/or a reaction scale to be used, and is preferably 0.5 to 100 hours in view of the reactivity.

Another example of the process for synthesizing the nucleophilic reagent, 6-(alkoxymethoxy)-3-hexenyl compound (3), comprises reacting the 6-halo-3-hexenyl alkoxymethyl ether compound (2) with an organolithium reagent in a solvent to obtain a 6-(alkoxymethoxy)-3-hexenyllithium compound (3: M=Li), as shown in the following chemical reaction formula. This process is hereinafter referred to as "conversion with an organolithium reagent")

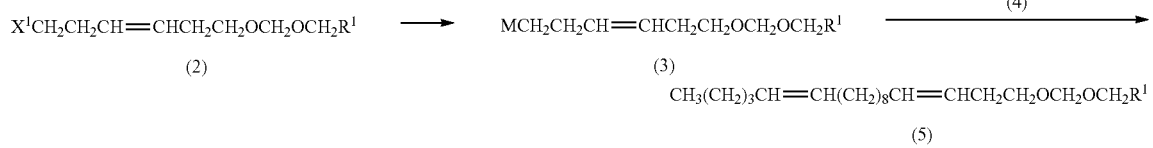

Preparation of the Nucleophilic Reagent, 6-(alkoxymethoxy)-3-hexenyl compound (3)

One example of the process for synthesizing the nucleophilic reagent, 6-(alkoxymethoxy)-3-hexenyl compound (3) comprises reacting the 6-halo-3-hexenyl alkoxymethyl ether compound (2) with magnesium in a solvent to obtain a 6-(alkoxymethoxy)-3-hexenylmagnesium halide compound (3: M=MgZ$^2$) which is a Grignard reagent, as shown in the following chemical reaction formula. This process is hereinafter referred to as "conversion with magnesium".

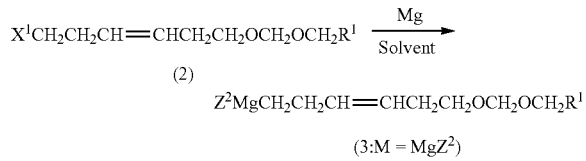

An amount of magnesium used in the conversion with magnesium is preferably 1.0 to 2.0 grams atom per mol of the 6-halo-3-hexenyl alkoxymethyl ether compound (2) in view of the completion of the reaction.

Examples of the solvent used in the conversion with magnesium include ethers such as tetrahydrofuran, diethyl ether, and 4-methyltetrahydropyran; and hydrocarbons such as toluene, xylene, and hexane. Ethers such as tetrahydrofuran, diethyl ether, and 4-methyltetrahydropyran, particularly tetrahydrofuran, is preferred in view of a reaction rate of the Grignard reagent formation.

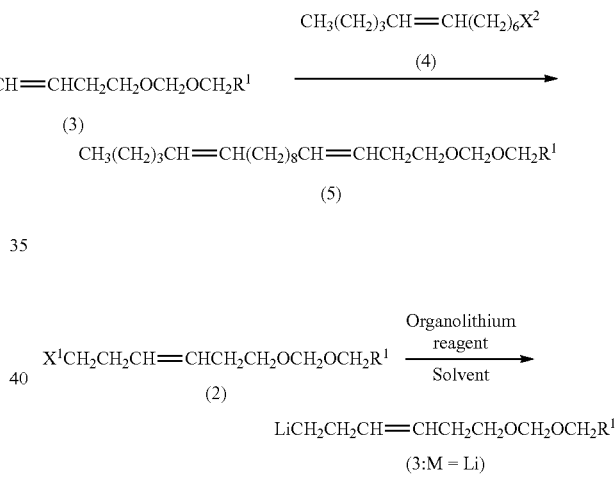

Examples of the organolithium reagent include linear organolithium reagents such as methyllithium, ethyllithium, n-propyllithium, n-butyllithium, and n-pentyllithium; and branched organolithium reagents such as sec-butyllithium and tert-butyllithium. Methyllithium, n-butyllithium, sec-butyllithium, and tert-butyllithium are preferred in view of the availability.

An amount of the organolithium reagent used is preferably 1.0 to 4.0 mol per mol of the 6-halo-3-hexenyl alkoxymethyl ether compound (2) in view of the reactivity.

Examples of the solvent used in the conversion with an organolithium reagent include ethers such as tetrahydrofuran, diethyl ether, and 4-methyltetrahydropyran; and hydrocarbons such as toluene, xylene, and hexane. A preferable solvent varies, depending on an organolithium reagent to be used. Generally, tetrahydrofuran, diethyl ether, toluene, or hexane is preferred in view of the reactivity.

The solvent may be used alone or in combination thereof, if necessary. The solvent may be commercially available one.

An amount of the solvent used is preferably 50 to 5,000 g, more preferably 100 to 3,000 g, per mol of the 6-halo-3-hexenyl alkoxymethyl ether compound (2) in view of the reactivity.

A reaction temperature of the conversion with an organolithium reagent varies, depending on a solvent to be used, and is preferably −78 to 25° C. in view of the reactivity.

A reaction time of the conversion with an organolithium reagent varies, depending on a solvent and/or a reaction scale to be used, and is preferably 0.5 to 100 hours in view of the reactivity.

The nucleophilic reagent, 6-(alkoxymethoxy)-3-hexenyl compound (3), will be explained below.

$R^1$ in the general formula (3) is as defined for the general formula (1).

M represents Li or $MgZ^2$, wherein $Z^2$ represents a halogen atom or a 6-(alkoxymethoxy)-3-hexenyl group. Examples of the halogen atom, $Z^2$, include a chlorine atom, a bromine atom, and an iodine atom.

Examples of the nucleophilic reagent, 6-(alkoxymethoxy)-3-hexenyl compound (3), include a nucleophilic reagent, (3E)-6-(alkoxymethoxy)-3-hexenyl compound of the following general formula (3-E), a nucleophilic reagent, (3Z)-6-(alkoxymethoxy)-3-hexenyl compound of the following general formula (3-Z), and a mixture thereof.

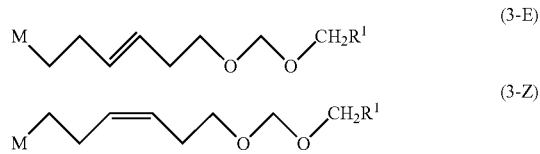

Specific examples of the nucleophilic reagent, (3E)-6-(alkoxymethoxy)-3-hexenyl compound (3-E), include the following compounds: (3E)-6-(alkoxymethoxy)-3-hexenyllithium compounds such as (3E)-6-(methoxymethoxy)-3-hexenyllithium, (3E)-6-(ethoxymethoxy)-3-hexenyllithium, (3E)-6-(propoxymethoxy)-3-hexenyllithium, (3E)-6-(butoxymethoxy)-3-hexenyllithium, (3E)-6-(pentyloxymethoxy)-3-hexenyllithium, (3E)-6-(hexyloxymethoxy)-3-hexenyllithium, (3E)-6-(heptyloxymethoxy)-3-hexenyllithium, (3E)-6-(octyloxymethoxy)-3-hexenyllithium, (3E)-6-(nonyloxymethoxy)-3-hexenyllithium, and (3E)-6-(decyloxymethoxy)-3-hexenyllithium; and (3E)-6-(alkoxymethoxy)-3-hexenylmagnesium halide compounds, including (3E)-6-(alkoxymethoxy)-3-hexenylmagnesium chloride compounds such as (3E)-6-(methoxymethoxy)-3-hexenylmagnesium chloride, (3E)-6-(ethoxymethoxy)-3-hexenylmagnesium chloride, (3E)-6-(propoxymethoxy)-3-hexenylmagnesium chloride, (3E)-6-(butoxymethoxy)-3-hexenylmagnesium chloride, (3E)-6-(pentyloxymethoxy)-3-hexenylmagnesium chloride, (3E)-6-(hexyloxymethoxy)-3-hexenylmagnesium chloride, (3E)-6-(heptyloxymethoxy)-3-hexenylmagnesium chloride, (3E)-6-(octyloxymethoxy)-3-hexenylmagnesium chloride, (3E)-6-(nonyloxymethoxy)-3-hexenylmagnesium chloride, and (3E)-6-(decyloxymethoxy)-3-hexenylmagnesium chloride; (3E)-6-(alkoxymethoxy)-3-hexenylmagnesium bromide compounds such as (3E)-6-(methoxymethoxy)-3-hexenylmagnesium bromide, (3E)-6-(ethoxymethoxy)-3-hexenylmagnesium bromide, (3E)-6-(propoxymethoxy)-3-hexenylmagnesium bromide, (3E)-6-(butoxymethoxy)-3-hexenylmagnesium bromide, (3E)-6-(pentyloxymethoxy)-3-hexenylmagnesium bromide, (3E)-6-(hexyloxymethoxy)-3-hexenylmagnesium bromide, (3E)-6-(heptyloxymethoxy)-3-hexenylmagnesium bromide, (3E)-6-(octyloxymethoxy)-3-hexenylmagnesium bromide, (3E)-6-(nonyloxymethoxy)-3-hexenylmagnesium bromide, and (3E)-6-(decyloxymethoxy)-3-hexenylmagnesium bromide; and (3E)-6-(alkoxymethoxy)-3-hexenylmagnesium iodide compounds such as (3E)-6-(methoxymethoxy)-3-hexenylmagnesium iodide, (3E)-6-(ethoxymethoxy)-3-hexenylmagnesium iodide, (3E)-6-(propoxymethoxy)-3-hexenylmagnesium iodide, (3E)-6-(butoxymethoxy)-3-hexenylmagnesium iodide, (3E)-6-(pentyloxymethoxy)-3-hexenylmagnesium iodide, (3E)-6-(hexyloxymethoxy)-3-hexenylmagnesium iodide, (3E)-6-(heptyloxymethoxy)-3-hexenylmagnesium iodide, (3E)-6-(octyloxymethoxy)-3-hexenylmagnesium iodide, (3E)-6-(nonyloxymethoxy)-3-hexenylmagnesium iodide, and (3E)-6-(decyloxymethoxy)-3-hexenylmagnesium iodide.

Among these, (3E)-6-(alkoxymethoxy)-3-hexenylmagnesium halide compounds such as (3E)-6-(alkoxymethoxy)-3-hexenylmagnesium chloride compounds are preferred in view of the availability.

Specific examples of the nucleophilic reagent, (3Z)-6-(alkoxymethoxy)-3-hexenyl compound (3-Z), include the following compounds: (3Z)-6-(alkoxymethoxy)-3-hexenyllithium compounds such as (3Z)-6-(methoxymethoxy)-3-hexenyllithium, (3Z)-6-(ethoxymethoxy)-3-hexenyllithium, (3Z)-6-(propoxymethoxy)-3-hexenyllithium, (3Z)-6-(butoxymethoxy)-3-hexenyllithium, (3Z)-6-(pentyloxymethoxy)-3-hexenyllithium, (3Z)-6-(hexyloxymethoxy)-3-hexenyllithium, (3Z)-6-(heptyloxymethoxy)-3-hexenyllithium, (3Z)-6-(octyloxymethoxy)-3-hexenyllithium, (3Z)-6-(nonyloxymethoxy)-3-hexenyllithium, and (3Z)-6-(decyloxymethoxy)-3-hexenyllithium; and (3Z)-6-(alkoxymethoxy)-3-hexenylmagnesium halide compounds, including (3Z)-6-(alkoxymethoxy)-3-hexenylmagnesium chloride compounds such as (3Z)-6-(methoxymethoxy)-3-hexenylmagnesium chloride, (3Z)-6-(ethoxymethoxy)-3-hexenylmagnesium chloride, (3Z)-6-(propoxymethoxy)-3-hexenylmagnesium chloride, (3Z)-6-(butoxymethoxy)-3-hexenylmagnesium chloride, (3Z)-6-(pentyloxymethoxy)-3-hexenylmagnesium chloride, (3Z)-6-(hexyloxymethoxy)-3-hexenylmagnesium chloride, (3Z)-6-(heptyloxymethoxy)-3-hexenylmagnesium chloride, (3Z)-6-(octyloxymethoxy)-3-hexenylmagnesium chloride, (3Z)-6-(nonyloxymethoxy)-3-hexenylmagnesium chloride, and (3Z)-6-(decyloxymethoxy)-3-hexenylmagnesium chloride; (3Z)-6-(alkoxymethoxy)-3-hexenylmagnesium bromide compounds such as (3Z)-6-(methoxymethoxy)-3-hexenylmagnesium bromide, (3Z)-6-(ethoxymethoxy)-3-hexenylmagnesium bromide, (3Z)-6-(propoxymethoxy)-3-hexenylmagnesium bromide, (3Z)-6-(butoxymethoxy)-3-hexenylmagnesium bromide, (3Z)-6-(pentyloxymethoxy)-3-hexenylmagnesium bromide, (3Z)-6-(hexyloxymethoxy)-3-hexenylmagnesium bromide, (3Z)-6-(heptyloxymethoxy)-3-hexenylmagnesium bromide, (3Z)-6-(octyloxymethoxy)-3-hexenylmagnesium bromide, (3Z)-6-(nonyloxymethoxy)-3-hexenylmagnesium bromide, and (3Z)-6-(decyloxymethoxy)-3-hexenylmagnesium bromide; and (3Z)-6-(alkoxymethoxy)-3-hexenylmagnesium iodide compounds such as (3Z)-6-(methoxymethoxy)-3-hexenylmagnesium iodide, (3Z)-6-(ethoxymethoxy)-3-hexenylmagnesium iodide, (3Z)-6-(propoxymethoxy)-3-hexenylmagnesium iodide, (3Z)-6-(butoxymethoxy)-3-hexenylmagnesium iodide, (3Z)-6-(pentyloxymethoxy)-3-hexenylmagnesium iodide, (3Z)-6-(hexyloxymethoxy)-3-hexenylmagnesium iodide, (3Z)-6-(heptyloxymethoxy)-3-hexenylmagnesium iodide, (3Z)-6-(octyloxymethoxy)-3-hexenylmagnesium iodide, (3Z)-6-(nonyloxymethoxy)-3-hexenylmagnesium iodide, and (3Z)-6-(decyloxymethoxy)-3-hexenylmagnesium iodide.

Among these, (3Z)-6-(alkoxymethoxy)-3-hexenylmagnesium halide compounds such as (3Z)-6-(alkoxymethoxy)-3-hexenylmagnesium chloride compounds are preferred in view of the availability.

One or plural species of the nucleophilic reagent, 6-(alkoxymethoxy)-3-hexenyl compound (3), may be used, if necessary.

The nucleophilic reagent, 6-(alkoxymethoxy)-3-hexenyl compound (3), may be commercially available one or may be prepared in house.

For example, a mixture of a nucleophilic reagent, (3E)-6-(alkoxymethoxy)-3-hexenyl compound (3-E), and a nucleophilic reagent, (3Z)-6-(alkoxymethoxy)-3-hexenyl compound (3-Z), will give a mixture of the (3E)-3,13-octadecadiene alkoxymethyl ether compound and the (3Z)-3,13-octadecadiene alkoxymethyl ether compound.

Preparation of 3,13-octadecadiene alkoxymethyl Ether Compound (5) Through a Coupling Reaction The nucleophilic reagent, 6-(alkoxymethoxy)-3-hexenyl compound (3), is subjected to a coupling reaction with a 12-halo-5-dodecene compound (4) to prepare the 3,13-octadecadiene alkoxymethyl ether compound (5).

First, the 12-halo-5-dodecene compound (4) will be explained below.

$X^2$ in the general formula (4) represents a halogen atom such as a fluorine atom, a chlorine atom, a bromine atom, or iodine atom. $X^2$ is preferably a chlorine atom, a bromine atom, or an iodine atom, more preferably a bromine atom or an iodine atom, in view of the reactivity.

Specific examples of the 12-halo-5-dodecene compound (4) include 12-fluoro-5-dodecene, 12-chloro-5-dodecene, 12-bromo-5-dodecene, and 12-iodo-5-dodecene. 12-Bromo-5-dodecene and 12-iodo-5-dodecene are preferred in view of the reactivity.

One or plural species of the 12-halo-5-dodecene compound (4) may be used, if necessary.

The 12-halo-5-dodecene compound (4) may be prepared in house, for example, by deprotonating a terminal alkyne of 1-hexyne, subjecting the product to a coupling reaction with a 1,6-dihaloalkane to synthesize a 12-halo-5-dodecyne compound, and then reducing the carbon-carbon triple bond into a carbon-carbon double bond. Alternatively, a 1-halo-3-octene compound is converted into an organometallic reagent, that is, a 3-dodecenyl nucleophilic reagent, which is then reacted with a 1,4-dihaloalkane compound to obtain the 12-halo-5-dodecene compound (4).

An amount of the nucleophilic reagent, 6-(alkoxymethoxy)-3-hexenyl compound (3), used in the coupling reaction is preferably 0.8 to 3.0 mol, more preferably 1.0 to 1.8 mol, per mol of the 12-halo-5-dodecene (4) in view of the economy.

A solvent may be incorporated in the coupling reaction, if necessary. Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); and nitriles such as acetonitrile and propionitrile. Toluene, tetrahydrofuran, 4-methyltetrahydropyran, or acetonitrile, particularly tetrahydrofuran, is preferred in view of the reactivity.

The solvent may be used alone or in combination thereof, if necessary. The solvent may be commercially available one.

An amount of the solvent used is preferably 30 to 5,000 g, more preferably 50 to 3,000 g, per mol of the 12-halo-5-dodecene compound (4) in view of the reactivity.

A catalyst may be incorporated in the coupling reaction, if necessary. Examples of the catalyst include copper compounds including cuprous halides such as cuprous chloride, cuprous bromide, and cuprous iodide, and cupric halides such as cupric chloride, cupric bromide, and cupric iodide; iron compounds such as iron(II) chloride, iron(III) chloride, iron(II) bromide, iron(III) bromide, iron(II) iodide, iron(III) iodide, and iron(III) acetylacetonate; silver compounds such as silver chloride, silver nitrate, and silver acetate; titanium compounds such as titanium tetrachloride, titanium tetrabromide, titanium(IV) methoxide, titanium(IV) ethoxide, titanium(IV) isopropoxide, and titanium (IV) oxide; palladium(II) compounds such as dichlorobis(triphenylphosphine)palladium and dichloro[1,1'-bis(diphenylphosphino)ferrocene]palladium; and nickel compounds such as nickel chloride, dichloro[1,2-bis(diphenylphosphino)ethane]nickel (II), and dichlorobis(triphenylphosphine)nickel(II). When the nucleophilic reagent, 6-(alkoxymethoxy)-3-hexenyl compound (3), is a Grignard reagent, that is, a 6-(alkoxymethoxy)-3-hexenylmagnesium halide compound (3: M=MgZ$^2$), copper compounds, particularly cuprous halides such as cuprous chloride, cuprous bromide, and cuprous iodide, are preferred in view of the reactivity and/or economy.

The catalyst may be used alone or in combination thereof, if necessary. The catalyst may be commercially available one.

An amount of the catalyst used is preferably 0.0003 to 0.300 mol, more preferably 0.003 to 0.100 mol, per mol of the 12-halo-5-dodecene compound (4) in view of the reaction rate and easy post-processing.

When an organolithium reagent is used in the coupling reaction, N,N,N',N'-tetramethylethylenediamine (TMEDA), hexamethylphosphoric triamide (HMPA), or N,N'-dimethylpropylene urea (DMPU) may be used to improve a reaction rate, if necessary.

When a catalyst is used in the coupling reaction, a co-catalyst may also be incorporated, if necessary. Examples of the co-catalyst include a trialkyl phosphite compound having 3 to 9 carbon atoms, such as triethyl phosphite; and an arylphosphine compound having 18 to 44 carbon atoms, such as triphenylphosphine, tritolylphosphine, or 2,2'-bis(diphenylphosphino)-1,1'-binaphthyl (BINAP). A trialkyl phosphite, particularly triethyl phosphite, is preferred in view of the reactivity.

The co-catalyst may be used alone or in combination thereof, if necessary. The co-catalyst may be commercially available one.

An amount of the co-catalyst used is preferably 0.0001 to 1.00 mol, more preferably 0.001 to 0.300 mol, per mol of the 12-halo-5-dodecene compound (4).

When a catalyst is used in the coupling reaction, a lithium halide may also be incorporated, if necessary. Examples of the lithium halide include lithium chloride, lithium bromide, and lithium iodide. Lithium chloride is preferred in view of the reactivity.

An amount of the lithium halide used in the coupling reaction is preferably 0.0001 to 1.00 mol, more preferably 0.001 to 0.300 mol, per mol of the 12-halo-5-dodecene compound (4), in view of the reactivity.

A reaction temperature of the coupling reaction varies, depending on the nucleophilic reagent, 6-(alkoxymethoxy)-3-hexenyl compound (3), and is preferably −78 to 80° C., more preferably −25 to 40° C. in view of the reactivity.

A reaction time of the coupling reaction varies, depending on a solvent and/or a reaction scale, and is preferably 0.5 to 100 hours in view of the reactivity.

The 3,13-octadecadiene alkoxymethyl ether compound (5) will be explained below.

$R^1$ in the general formula (5) is as defined for the general formula (1).

Specific examples of the 3,13-octadecadiene alkoxymethyl ether compound (5) include the following compounds:

(3Z,13Z)-3,13-octadecadiene alkoxymethyl ether compounds such as (3Z,13Z)-3,13-octadecadiene methoxymethyl ether, (3Z,13Z)-3,13-octadecadiene ethoxymethyl ether, (3Z,13Z)-3,13-octadecadiene propoxymethyl ether, (3Z,13Z)-3,13-octadecadiene butoxymethyl ether, (3Z,13Z)-3,13-octadecadiene pentyloxymethyl ether, (3Z,13Z)-3,13-octadecadiene hexyloxymethyl ether, (3Z,13Z)-3,13-octadecadiene heptyloxymethyl ether, (3Z,13Z)-3,13-octadecadiene octyloxymethyl ether, (3Z,13Z)-3,13-octadecadiene nonyloxymethyl ether, (3Z,13Z)-3,13-octadecadiene decyloxymethyl ether, and (3Z,13Z)-3,13-octadecadiene benzyloxymethyl ether;

(3Z,13E)-3,13-octadecadiene alkoxymethyl ether compounds such as (3Z,13E)-3,13-octadecadiene methoxymethyl ether, (3Z,13E)-3,13-octadecadiene ethoxymethyl ether, (3Z,13E)-3,13-octadecadiene propoxymethyl ether, (3Z,13E)-3,13-octadecadiene butoxymethyl ether, (3Z,13E)-3,13-octadecadiene pentyloxymethyl ether, (3Z,13E)-3,13-octadecadiene hexyloxymethyl ether, (3Z,13E)-3,13-octadecadiene heptyloxymethyl ether, (3Z,13E)-3,13-octadecadiene octyloxymethyl ether, (3Z,13E)-3,13-octadecadiene nonyloxymethyl ether, (3Z,13E)-3,13-octadecadiene decyloxymethyl ether, and (3Z,13E)-3,13-octadecadiene benzyloxymethyl ether;

(3E,13Z)-3,13-octadecadiene alkoxymethyl ether compounds such as (3E,13Z)-3,13-octadecadiene methoxymethyl ether, (3E,13Z)-3,13-octadecadiene ethoxymethyl ether, (3E,13Z)-3,13-octadecadiene propoxymethyl ether, (3E,13Z)-3,13-octadecadiene butoxymethyl ether, (3E,13Z)-3,13-octadecadiene pentyloxymethyl ether, (3E,13Z)-3,13-octadecadiene hexyloxymethyl ether, (3E,13Z)-3,13-octadecadiene heptyloxymethyl ether, (3E,13Z)-3,13-octadecadiene octyloxymethyl ether, (3E,13Z)-3,13-octadecadiene nonyloxymethyl ether, (3E,13Z)-3,13-octadecadiene decyloxymethyl ether, and (3E,13Z)-3,13-octadecadiene benzyloxymethyl ether; and (3E,13E)-3,13-octadecadiene alkoxymethyl ether compounds such as (3E,13E)-3,13-octadecadiene methoxymethyl ether, (3E,13E)-3,13-octadecadiene ethoxymethyl ether, (3E,13E)-3,13-octadecadiene propoxymethyl ether, (3E,13E)-3,13-octadecadiene butoxymethyl ether, (3E,13E)-3,13-octadecadiene pentyloxymethyl ether, (3E,13E)-3,13-octadecadiene hexyloxymethyl ether, (3E,13E)-3,13-octadecadiene heptyloxymethyl ether, (3E,13E)-3,13-octadecadiene octyloxymethyl ether, (3E,13E)-3,13-octadecadiene nonyloxymethyl ether, (3E,13E)-3,13-octadecadiene decyloxymethyl ether, and (3E,13E)-3,13-octadecadiene benzyloxymethyl ether.

Among these, a 3,13-octadecadiene methoxymethyl ether compound, a 3,13-octadecadiene ethoxymethyl ether compound, a 3,13-octadecadiene butoxymethyl ether compound, and a 3,13-octadecadiene benzyloxymethyl ether compound are preferred in view of the economy.

Preparation of 3,13-octadecadien-1-ol compound (6) through dealkoxymethylation Reaction The 3,13-octadecadien-1-ol compound (6) may be prepared by dealkoxymethylating the 3,13-octadecadiene alkoxymethyl ether compound (5), as shown in the following chemical reaction formula.

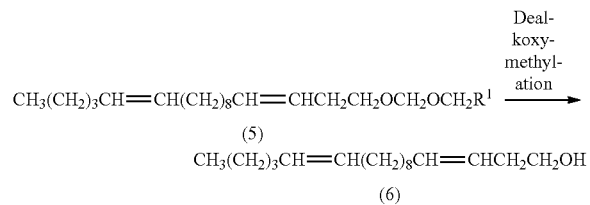

One or plural species of the 3,13-octadecadiene alkoxymethyl ether compound (5) may be used in the dealkoxymethylation reaction, if necessary.

For example, a mixture of a (3Z,13Z)-3,13-octadecadiene alkoxymethyl ether compound (5) and a (3Z,13E)-3,13-octadecadiene alkoxymethyl ether compound (5) will give a mixture of (3Z,13Z)-3,13-octadecadien-1-ol (6) and (3Z,13E)-3,13-octadecadien-1-ol (6).

Optimal conditions of the dealkoxymethylation reaction varies, depending on $R^1$. For example, when $R^1$ is a phenyl group, the dealkoxymethylation may be carried out under Birch reduction conditions in which sodium is used in liquid ammonia. When $R^1$ is a hydrogen atom or an n-alkyl group such as a methyl group, the dealkoxymethylation may be carried out using an acid or an alcohol compound (8) mentioned below.

Examples of the acid include inorganic acids such as hydrochloric acid and hydrobromic acid; sulfonic acids such as p-toluenesulfonic acid and benzenesulfonic acid; organic acids such as trifluoroacetic acid, acetic acid, formic acid, and oxalic acid; and Lewis acids such as iodotrimethylsilane and titanium tetrachloride. p-Toluenesulfonic acid, benzenesulfonic acid, hydrochloric acid, and hydrobromic acid, particularly p-toluenesulfonic acid, hydrochloric acid, and hydrobromic acid, are preferred in view of the suppression of side reactions.

The acid may be used alone or in combination thereof, if necessary. The acid may be commercially available one.

An amount of the acid used is preferably 0.0001 to 10.0 mol, more preferably 0.001 to 1.0 mol, per mol of the 3,13-octadecadiene alkoxymethyl ether compound (5).

The alcohol compound (8) is represented by the following general formula (8):

$R^2$ represents a monovalent hydrocarbon group having 1 to 15 carbon atoms, preferably 1 to 6 carbon atoms, in view of the price or availability. Examples of the monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched saturated hydrocarbon groups such as an isopropyl group, a 2-isobutyl group, and a 2-methylbutyl group; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and isomers thereof. A part of the hydrogen atoms of the hydrocarbon group may be substituted with a methyl group, an ethyl group, or a hydroxyl group.

The monovalent hydrocarbon group is preferably a methyl group, an ethyl group, an n-propyl group, or an n-butyl group in view of the handling.

Examples of the alcohol compound (8) include linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; branched alcohols such as isopropanol and 2-butanol; and diols such as ethyleneglycol, propyleneglycol, 2-methyl-1,3-propanediol, 2,2-dimethyl-1,3-propanediol, 1,2-dimethyl-1,3-propanediol, 1,3-dimethyl-1,3-propanediol, and 2-methyl-1,4-butanediol. Methanol and ethanol, particularly methanol, are preferred in view of the reactivity.

The alcohol compound (8) may be used alone or in combination thereof, if necessary.

The alcohol compound (8) may be commercially available one.

An amount of the alcohol compound (8) used is preferably 1 to 1,000 mol, more preferably 1 to 100 mol, per mol of the 3,13-octadecadiene alkoxymethyl ether compound (5) in view of the reactivity.

A solvent other than the alcohol compound (8) may be used in the dealkoxymethylation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate.

The solvent may be used alone or in combination thereof, if necessary. The solvent may be commercially available one.

An amount of the solvent used in the dealkoxymethylation reaction is preferably 0 to 2,000 g, more preferably 0 to 500 g, per mol of the 3,13-octadecadiene alkoxymethyl ether compound (5).

The solvent occupies a space of a reactor to reduce a space for starting material, resulting in a decreased productivity. Therefore, the dealkoxymethylation may be carried out without a solvent.

A reaction temperature of the dealkoxymethylation varies, depending on a 3,13-octadecadiene alkoxymethyl ether compound (5) to be used, and is preferably −5 to 180° C. in view of the reactivity.

A reaction time of the dealkoxymethylation varies, depending on a 3,13-octadecadiene alkoxymethyl ether compound (5) and/or a reaction scale, and is preferably 0.5 to 100 hours in view of the reactivity.

In the dealkoxymethylation a by-produced alkoxymethoxymethane may be distilled off from the reaction system, if necessary, whereby the equilibrium is shifted to the product side to reduce the reaction time.

Specific examples of the 3,13-octadecadien-1-ol compound (6) include (3Z,13Z)-3,13-octadecadien-1-ol, (3Z,13E)-3,13-octadecadien-1-ol, (3E,13Z)-3,13-octadecadien-1-ol, and (3E,13E)-3,13-octadecadien-1-ol.

Preparation of 3,13-octadecadienyl acetate Compound (7) Through Acetylation

The 3,13-octadecadienyl acetate compound (7) may be prepared by acetylating the 3,13-octadecadien-1-ol compound (6), as shown in the following chemical reaction formula.

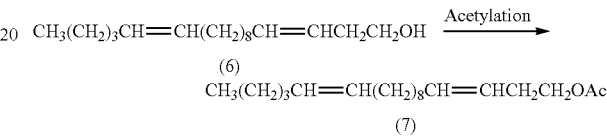

One or plural species of the 3,13-octadecadien-1-ol compound (6) may be used in the acetylation, if necessary.

For example, a mixture of (3Z,13Z)-3,13-octadecadien-1-ol (6) and (3Z,13E)-3,13-octadecadien-1-ol (6) will give a mixture of (3Z,13Z)-3,13-octadecadienyl acetate (7) and (3Z,13E)-3,13-octadecadienyl acetate (7).

The acetylation may be carried out using an acetylating agent.

Examples of the acetylating agent include acid anhydrides such as acetic anhydride; acetyl halide compounds such as acetyl chloride, acetyl bromide, and acetyl iodide; and acetic ester compounds such as methyl acetate and ethyl acetate. Acetic anhydride and acetyl halide compounds are preferred in view of the availability.

An amount of the acetylating agent used is preferably 1.0 to 10.0 mol, more preferably 1.0 to 5.0 mol, per mol of the 3,13-octadecadien-1-ol compound (6) in view of the reactivity and economy.

An acid or base may be incorporated in the acetylation, if necessary.

Examples of the acid include mineral acids such as hydrochloric acid, sulfuric acid, and nitric acid; aromatic sulfonic acids such as benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, magnesium chloride, magnesium bromide, titanium tetrachloride, titanium tetrabromide, titanium(IV) methoxide, titanium(IV) ethoxide, titanium (IV) isopropoxide, and titanium (IV) oxide.

The acid may be used alone or in combination thereof, if necessary.

An amount of the acid used is preferably 0.001 to 3.00 mol, more preferably 0.01 to 1.50 mol, per mol of the 3,13-octadecadien-1-ol compound (6) in view of the reactivity and economy.

Examples of the base include trialkylamine compounds such as trimethylamine, triethylamine, and N,N-diisopropylethylamine; cyclic amine compounds such as piperidine, pyrrolidine, and 1,8-diazabicyclo[5.4.0]-7-undecene (DBU); aromatic amine compounds such as pyridine, lutidine, N,N-dimethylaniline, N,N-diethylaniline, N,N-dibutylaniline, and 4-dimethylaminopyridine; and metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide.

The base may be used alone or in combination thereof, if necessary.

An amount of the base used is preferably 0.010 to 10.0 mol, more preferably 1.0 to 5.0 mol, per mol of the 3,13-octadecadien-1-ol compound (6), in view of the reactivity and economy.

A solvent may be incorporated in the acetylation, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. Hydrocarbons such as toluene and xylene are preferred in view of the reactivity.

The solvent may be used alone or in combination thereof, if necessary. The solvent may be commercially available one.

The acetylation may be carried out with or without a solvent, s needed.

An amount of the solvent used in the acetylation is preferably 0 to 2,000 g, more preferably 0 to 500 g, per mol of the 3,13-octadecadien-1-ol compound (6).

The 3,13-octadecadienyl acetate compound (7) will be explained below.

In the formula (7), Ac represents an acetyl group.

EXAMPLES

The present invention will be described with reference to the following Examples. It should be noted that the present invention is not limited to or by the Examples.

The term "purity" as used herein means an area percentage in gas chromatography (GC), unless otherwise specified. The term "production ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-WAX (sp-2331), 0.25 μm×0.25 mmφ×30 m; carrier gas: He (1.55 mL/min), detector: FID; column temperature: 150° ° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]
÷[(weight of a starting material in a reaction×% GC)/molecular weight of a starting material]}× 100

THF represents tetrahydrofuran, GBL represents γ-butyrolactone, P-2Ni represents P-2 nickel boride, Ms represents a methanesulfonyl group, Me represents a methyl group, Et represents an ethyl group, Ac represents an acetyl group, and Ph represents a phenyl group.

Example 1: Preparation of 6-hydroxy-3-hexynyl methoxymethyl ether (10: R¹=H)

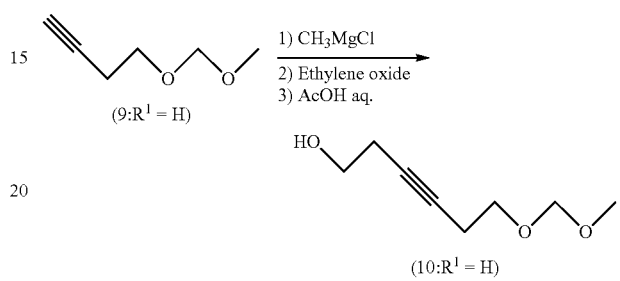

Methylmagnesium chloride (366.84 g, 4.91 mol) and tetrahydrofuran (1530.16 g) were placed in a reactor at room temperature and stirred at 20 to 25° C. for 4 minutes. After the completion of the stirring, 3-butynyl methoxymethyl ether (9: R¹=H) (517.25 g, 4.50 mol, purity 99.30%) was added dropwise to the reactor at 25 to 60° C. After the completion of the dropwise addition, the reaction mixture was stirred at 60 to 70° C. for 5 hours. Subsequently, ethylene oxide (257.69 g, 5.85 mol) was added dropwise at 40 to 60° C. After the completion of the dropwise addition, the reaction mixture was stirred at 60 to 65° ° C. for 3.5 hours. Next, a solution of acetic acid (800.00 g) in water (1600.00 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain 6-hydroxy-3-hexynyl methoxymethyl ether (10: R¹=H) (635.95 g, 3.91 mol, purity 97.16%, b.p.=105.6 to 125.1° C./0.40 kPa (3.0 mmHg)) in a yield of 86.80%.

The following are spectrum data of the 6-hydroxy-3-hexynyl methoxymethyl ether (10: R¹=H) thus prepared.

Nuclear magnetic resonance spectrum: $^1$H-NMR (500 MHz, CDCl$_3$): δ=2.37-2.42 (2H, m), 2.42-2.47 (2H, m), 3.34 (3H, s), 3.60 (2H, t, J=6.5 Hz), 3.64 (2H, t, J=6.2 Hz), 4.62 (2H, s); $^{13}$C-NMR (500 MHz, CDCl$_3$): δ=20.16, 23.03, 55.17, 61.10, 66.17, 77.77, 79.03, 96.23.

Mass spectrum: EI-mass spectrum (70 eV): m/z 157 (M$^+$−1), 127, 109, 97, 75, 45.

Infrared absorption spectrum (D-ATR): νmax=3427, 2936, 2885, 1383, 1208, 1150, 1111, 1072, 1040, 918, 849.

Example 2: Preparation of (3Z)-6-hydroxy-3-hexenyl methoxymethyl ether (1: R¹=H)

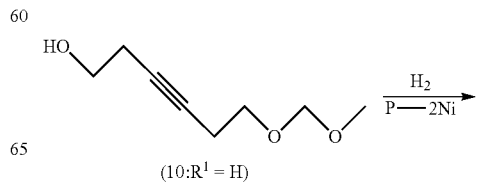

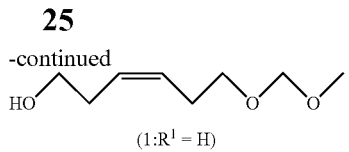
(1:R¹ = H)

The 6-hydroxy-3-hexynyl methoxymethyl ether (10: R¹=H) (635.95 g, 3.91 mol, purity 97.16%) obtained in Example 1 and P-2 Ni catalyst (108.60 g) were placed in a reactor at room temperature. The reactor was purged with a hydrogen gas at 45 to 55° C. for 7.5 hours with stirring. The conversion was confirmed to be 100%, and then water (170.94 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-6-hydroxy-3-hexenyl methoxymethyl ether (1: R¹=H) (612.16 g, 3.62 mol, purity 94.74%, b.p.=107.2 to 111.0° C./0.40 kPa (3.0 mmHg)) in a yield of 92.58%.

The following are spectrum data of the (3Z)-6-hydroxy-3-hexenyl methoxymethyl ether (1: R¹=H) thus prepared.

Nuclear magnetic resonance spectrum: ¹H-NMR (500 MHZ, CDCl₃): δ=2.32 (2H, dt, J=6.9 Hz, 6.9 Hz), 2.37 (2H, dt, J=7.3 Hz, 7.3 Hz), 3.33 (3H, s), 3.54 (2H, t, J=6.5 Hz), 3.61 (2H, t, J=6.5 Hz), 4.59 (2H, s), 5.46-5.59 (2H, m); ¹³C-NMR (500 MHZ, CDCl₃): δ=27.82, 30.69, 55.13, 61.84, 66.87, 96.19, 127.83, 129.16.

Mass spectrum: EI-mass spectrum (70 eV): m/z 159 (M⁺-1), 130, 111, 100, 81, 68, 55, 45.

Infrared absorption spectrum (D-ATR): νmax=3423, 2932, 2883, 1442, 1404, 1150, 1109, 1035, 919, 725.

Example 3: Preparation of (3E)-6-hydroxy-3-hexenyl methoxymethyl ether (1: R¹=H)

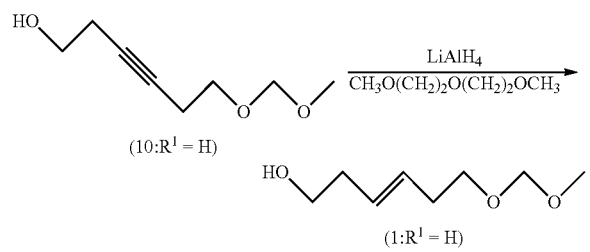

Lithium aluminum hydride (42.50 g, 1.12 mol) and diethyleneglycol dimethyl ether (666.24 g) were placed in a reactor at room temperature and stirred at 50 to 55° C. for 15 minutes. After the completion of the stirring, the 6-hydroxy-3-hexynyl methoxymethyl ether (260.85 g, 1.60 mol, purity 97.03%) obtained according to Example 1 was added dropwise at 50 to 60° C. and stirred at 130 to 135° C. for 20 hours. After cooling to 20 to 25° C., tetrahydrofuran (2508.78 g), water (42.50 g), an aqueous solution (170.03 g) of sodium hydroxide (0.16 mol), and Celite (529.51 g) were sequentially added, and stirred for 12 hours. After the completion of the stirring, the reaction mixture was filtered to obtain the organic phase. The organic phase thus obtained was concentrated at a reduced pressure, and the concentrate was subjected to distillation at a reduced pressure to obtain (3E)-6-hydroxy-3-hexenyl methoxymethyl ether (1: R¹=H) (235.15 g, 1.44 mol, purity 98.13%, b.p.=104.3 to 105.6° C./0.40 kPa (3.0 mmHg)) in a yield of 90.02%.

The following are spectrum data of the (3E)-6-hydroxy-3-hexenyl methoxymethyl ether (1: R¹=H) thus prepared.

Nuclear magnetic resonance spectrum: 1H-NMR (500 MHZ, CDCl₃): δ=1.89 (1H, br. s), 2.25 (2H, ddt, J=0.8 Hz, 6.5 Hz, 6.5 Hz), 2.30 (2H, ddt, J=0.8 Hz, 6.9 Hz, 6.9 Hz), 3.33 (3H, s), 3.54 (2H, t, J=6.9 Hz), 3.60 (2H, t, J=6.5 Hz), 4.59 (2H, s), 5.43-5.58 (2H, m); ¹³C-NMR (500 MHz, CDCl₃): δ=33.02, 35.96, 55.09, 61.77, 67.24, 96.29, 128.27, 129.91.

Mass spectrum: EI-mass spectrum (70 eV): m/z 159 (M⁺-1), 130, 100, 81, 68, 55, 45.

Infrared absorption spectrum (D-ATR): νmax=3410, 2931, 2885, 1442, 1383, 1211, 1150, 1110, 1043, 970, 919.

Example 4: Preparation of (3Z)-6-hydroxy-3-hexenyl butoxymethyl ether (1: R¹=CH₂CH₂CH₃)

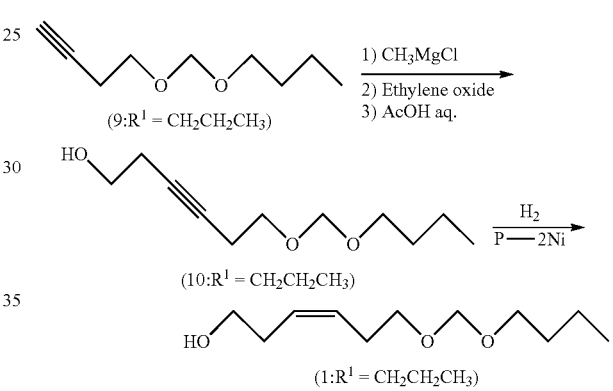

The procedures of Examples 1 and 2 were repeated with the exception that 3-butynyl butoxymethyl ether (9: R¹=CH₂CH₂CH₃) (276.94 g, 1.52 mol, purity 85.75%) was used instead of 3-butynyl methoxymethyl ether as a starting material, so that (3Z)-6-hydroxy-3-hexenyl butoxymethyl ether (1: R¹=CH₃CH₂CH₂) (251.00 g, 1.20 mol, purity 96.42%, b.p.=122.0 to 126.9° C./0.40 kPa (3.0 mmHg)) was obtained in a yield of 78.71% after the two steps.

The following are spectrum data of the (3Z)-6-hydroxy-3-hexenyl butoxymethyl ether (1: R¹=CH₃CH₂CH₂) thus prepared.

Nuclear magnetic resonance spectrum: 1H-NMR (500 MHz, CDCl₃): δ=0.91 (3H, t, J=7.3 Hz), 1.31-1.41 (2H, m), 1.51-1.59 (2H, m), 2.17 (1H, br. s), 2.33 (2H, dt, J=6.7 Hz, 6.7 Hz), 2.37 (2H, dt, J=6.7 Hz, 6.7 Hz), 3.50 (2H, t, J=6.5 Hz), 3.56 (2H, t, J=6.5 Hz), 3.62 (2H, t, J=6.1 Hz), 4.64 (2H, s), 5.50 (1H, dtt, J=10.7 Hz, 7.3 Hz, 1.5 Hz), 5.56 (1H, dtt, J=11.1 Hz, 7.3 Hz, 1.2 Hz); ¹³C-NMR (500 MHz, CDCl₃): δ=13.81, 19.31, 27.85, 30.70, 31.70, 61.87, 66.83, 67.61, 95.08, 127.80, 129.32.

Mass spectrum: EI-mass spectrum (70 eV): m/z 201 (M⁺-1), 185, 129, 111, 99, 87, 69, 57, 41, 29.

Infrared absorption spectrum (D-ATR): νmax=3431, 2957, 2933, 2873, 1465, 1380, 1146, 1115, 1045, 828, 725.

Example 5: Preparation of (3Z)-6-hydroxy-3-hexenyl benzyloxymethyl ether (1: R¹=Ph)

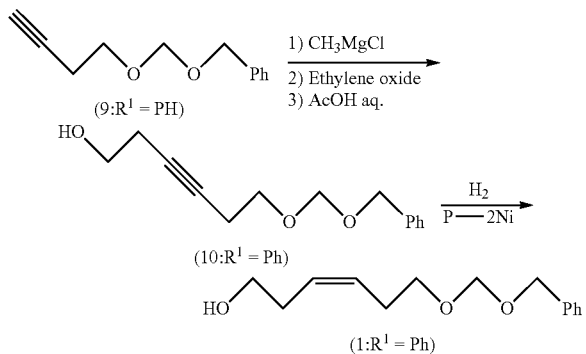

The procedures of Examples 1 and 2 were repeated with the exception that 3-butynyl benzyloxymethyl ether (9: R¹=Ph) (190.79 g, 0.95 mol, purity 95.21%) was used instead of 3-butynyl methoxymethyl ether as a starting material, so that (3Z)-6-hydroxy-3-hexenyl benzyloxymethyl ether (1: R¹=Ph) (163.56 g, 0.65 mol, purity 94.20%, b.p.=160.0 to 163.7° C./0.40 kPa (3.0 mmHg)) was obtained in a yield of 68.28%.

The following are spectrum data of the (3Z)-6-hydroxy-3-hexenyl benzyloxymethyl ether (1: R¹=Ph) thus prepared.

Nuclear magnetic resonance spectrum: 1H-NMR (500 MHz, CDCl₃): δ=2.06 (1H, br. s), 2.35 (2H, dt, J=6.6 Hz, 6.6 Hz), 2.40 (2H, dt, J=6.6 Hz, 6.6 Hz), 3.64 (2H, t, J=6.5 Hz), 3.64 (2H, t, J=6.2 Hz), 4.60 (2H, s), 4.76 (2H, s), 5.52 (1H, dtt, J=10.7 Hz, 7.3 Hz, 1.6 Hz), 5.59 (1H, J=11.1 Hz, 7.3 Hz, 1.1 Hz), 7.27-7.37 (5H, m); ¹³C-NMR (500 MHz, CDCl₃): δ=27.85, 30.73, 61.90, 67.13, 69.39, 94.49, 127.65, 127.85, 127.87, 128.36, 129.28, 137.81.

Mass spectrum: EI-mass spectrum (70 eV): m/z 235 (M⁺−1), 218, 206, 160, 129, 108, 91, 77, 65, 53, 41, 29.

Infrared absorption spectrum (D-ATR): νmax=3420, 2939, 2877, 1454, 1379, 1164, 1110, 1046, 1027, 737, 698.

Example 6: Preparation of (3Z)-6-chloro-3-hexenyl methoxymethyl ether (2: R¹=H, X¹=Cl)

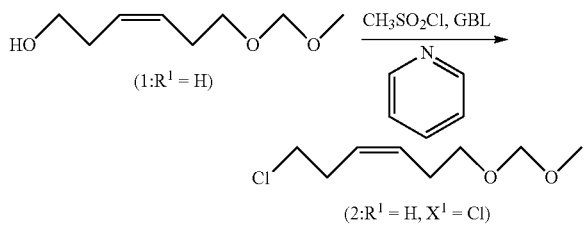

The (3Z)-6-hydroxy-3-hexenyl methoxymethyl ether (1: R¹=H) (541.14 g, 3.20 mol, purity 94.74%) obtained in Example 2, pyridine (455.62 g, 5.76 mol), and GBL (960.00 g) were placed in a reactor and stirred at 0 to 10° C. for 26 minutes.

Subsequently, methanesulfonyl chloride (513.18 g, 4.48 mol) was added dropwise at 0 to 10° C. After the completion of the dropwise addition, the reaction mixture was heated to 60 to 65° C. and stirred for 5 hours. After the completion of the stirring, water (1280.00 g) and hexane (1280.00 g) were sequentially added to the reaction mixture, followed by phase separation. The aqueous phase was removed to obtain the organic phase. The organic phase thus obtained was washed with a solution of acetic acid (160.00 g) in water (1280.00 g), and then washed with a solution of sodium bicarbonate (80.00 g) in water (1280.00 g). The organic phase thus obtained was concentrated at a reduced pressure. The concentrate was subjected to distillation at a reduced pressure to obtain (3Z)-6-chloro-3-hexenyl methoxymethyl ether (2: R¹=H, X¹=Cl) (496.72 g, 2.71 mol, purity 97.33%, b.p.=80.0 to 82.9° C./0.40 kPa (3.0 mmHg)) in a yield of 84.57%.

The following are spectrum data of the (3Z)-6-chloro-3-hexenyl methoxymethyl ether (2: R¹=H, X¹=Cl) thus prepared.

Nuclear magnetic resonance spectrum: 1H-NMR (500 MHz, CDCl₃): δ=2.36 (2H, dt, J=6.5 Hz, 6.5 Hz), 2.53 (2H, dt, J=7.1 Hz, 7.1 Hz), 3.35 (3H, s), 3.51 (2H, t, J=6.9 Hz), 3.54 (2H, t, J=6.9 Hz), 4.61 (2H, s), 5.49 (1H, dtt, J=10.7 Hz, 7.3 Hz, 1.5 Hz), 5.57 (1H, dtt, J=10.7 Hz, 7.3 Hz, 1.6 Hz); ¹³C-NMR (500 MHZ, CDCl₃): δ=28.03, 30.71, 44.01, 55.12, 66.98, 96.32, 127.08, 128.98.

Mass spectrum: EI-mass spectrum (70 eV): m/z 177 (M⁺−1), 147, 129, 112, 97, 75, 65, 55, 45, 29.

Infrared absorption spectrum (D-ATR): νmax=2951, 2884, 1444, 1381, 1296, 1209, 1148, 1111, 1036, 919, 738, 661.

Example 7: Preparation of (3Z,13Z)-3,13-octadiene methoxymethyl ether (5: R¹=H)

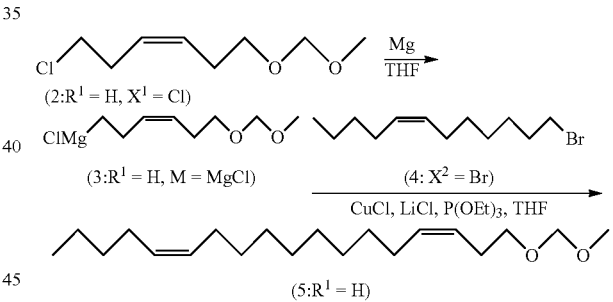

Magnesium (15.24 g, 0.63 grams atom) and tetrahydrofuran (171.00 g) were placed in a reactor at room temperature and stirred at 60 to 65° C. for 9 minutes. After the completion of the stirring, the (3Z)-6-chloro-3-hexenyl methoxymethyl ether (2: R¹=H, X¹=Cl) (109.86 g, 0.60 mol, purity 97.33%) obtained in Example 6 was added dropwise at 60 to 75° C. After the completion of the dropwise addition, the reaction mixture was stirred at 75 to 80° C. for 2 hours to prepare (3Z)-6-(methoxymethoxy)-3-hexenylmagnesium chloride (3: R¹=H, M=MgCl).

Subsequently, cuprous chloride (0.64 g, 0.0065 mol), lithium chloride (0.44 g, 0.010 mol), triethyl phosphite (6.39 g, 0.038 mol), tetrahydrofuran (114.00 g), and (5Z)-12-bromo-5-dodecene (4: X²=Br) (140.92 g, 0.57 mol, purity 100%) were placed in another reactor, and the (3Z)-6-(methoxymethoxy)-3-hexenylmagnesium chloride (3: R¹=H, M=MgCl) prepared above was added dropwise at 15 to 30° C. After the completion of the dropwise addition, the reaction mixture was stirred at 15 to 25° C. for 2.5 hours. Next, a solution of ammonium chloride (6.28 g) in water (163.01 g) and hydrochloric acid (11.98 g, 0.066 mol of hydrogen chloride) were added sequentially to the reaction mixture, followed by phase separation and removal of the aqueous phase. The organic phase thus obtained was concentrated at a reduced pressure, and the concentrate was subjected to distillation at a reduced pressure to obtain (3Z,13Z)-3,13-octadiene methoxymethyl ether (5: $R^1$=H) (163.39 g, 0.49 mol, purity 92.36%, b.p.=150.5 to 156.1° C./0.40 kPa (3.0 mmHg)) in a yield of 85.27%.

The following are spectrum data of the (3Z,13Z)-3,13-octadiene methoxymethyl ether (5: $R^1$=H) thus prepared.

Nuclear magnetic resonance spectrum: 1H-NMR (500 MHZ, CDCl$_3$): δ=0.89 (3H, t, J=7.3 Hz), 1.24-1.38 (16H, m), 1.96-2.07 (6H, m), 2.34 (2H, q-like, J=6.9 Hz), 3.36 (3H, s), 3.53 (2H, t, J=7.3 Hz), 4.62 (2H, s), 5.32-5.41 (3H, m), 5.47 (1H, dtt, J=10.7 Hz, 7.3 Hz, 1.5 Hz); $^{13}$C-NMR (500 MHZ, CDCl$_3$): δ=13.97, 22.33, 26.89, 27.16, 27.33, 27.88, 29.27, 29.49, 29.59, 29.74, 31.95, 55.10, 67.40, 96.32, 125.34, 129.82, 129.84, 132.19.

Mass spectrum: EI-mass spectrum (70 eV): m/z 310 (M$^+$), 278, 248, 219, 151, 135, 109, 81, 45, 29.

Infrared absorption spectrum (D-ATR): νmax=2925, 2854, 1465, 1379, 1151, 1111, 1074, 1037, 920, 723.

Example 8: Preparation of (3Z,13Z)-3,13-octadecadien-1-ol (6)

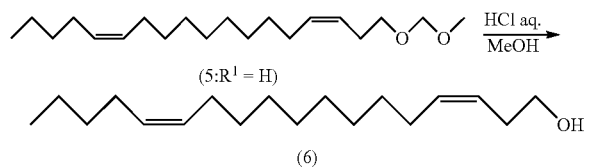

The (3Z,13Z)-3,13-octadiene methoxymethyl ether (5: $R^1$=H) (157.99 g, 0.47 mol, purity 92.36%) obtained in Example 7, methanol (234.95 g, 7.33 mol), and 20% hydrochloric acid (23.50 g, 0.13 mol of hydrogen chloride) were placed in a reactor equipped with a distillation tower, and the reaction mixture was heated to 60° C. and stirred for 1 hour. After the completion of the stirring, the internal temperature was raised to 65 to 70° C. to distill off a mixture of by-produced dimethoxymethane and methanol from the distillation tower. The reaction mixture was sampled during the reaction. After the conversion was confirmed to be 100%, water (140.97 g) was added to the reaction mixture, followed by phase separation. The aqueous phase was removed to obtain the organic phase. The organic phase thus obtained was subjected to distillation at a reduced pressure to obtain (3Z,13Z)-3,13-octadecadien-1-ol (6) (127.12 g, 0.44 mol, purity 91.56%, b.p.=160.0 to 165.8° C./0.40 kPa (3.0 mmHg)) in a yield of 92.96%.

The following are spectrum data of the (3Z,13Z)-3,13-octadecadien-1-ol (6) thus prepared.

Nuclear magnetic resonance spectrum: 1H-NMR (500 MHZ, CDCl$_3$): δ=0.89 (3H, t, J=7.3 Hz), 1.24-1.38 (16H, m), 1.54 (1H, br. s), 1.98-2.09 (6H, m), 2.32 (2H, q-like, J=6.7 Hz), 3.63 (2H, t, J=6.5 Hz), 5.30-5.40 (3H, m), 5.55 (1H, dtt, J=10.7 Hz, 7.3 Hz, 1.5 Hz); $^{13}$C-NMR (500 MHZ, CDCl$_3$): δ=13.96, 22.32, 26.89, 27.16, 27.34, 29.26, 29.47, 29.68, 29.73, 30.77, 31.94, 62.31, 124.91, 129.84, 133.51.

Mass spectrum: EI-mass spectrum (70 eV): m/z 266 (M$^+$), 248, 222, 208, 194, 177, 163, 149, 135, 121, 109, 95, 81, 55, 41.

Infrared absorption spectrum (D-ATR): νmax=3333, 2925, 2854, 1465, 1049, 722.

Example 9: Preparation of (3Z,13Z)-3,13-octadecadienyl acetate (7)

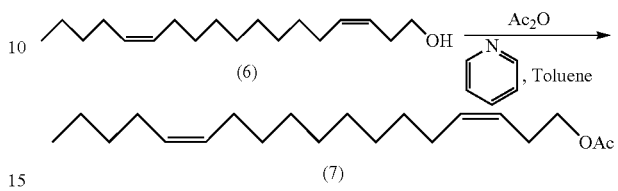

The (3Z,13Z)-3,13-octadecadien-1-ol (6) (104.31 g, 0.36 mol, purity 91.56%) obtained in Example 8, toluene (78.56 g), and pyridine (53.86 g, 0.68 mol) were placed in a reactor at room temperature and stirred at 15 to 25° C. for 2 minutes. After the completion of the stirring, acetic anhydride (153.14 g, 0.54 mol) was added dropwise at 20 to 40° C. and stirred at 30 to 35° ° C. for 6.5 hours. Next, water (94.14 g) was added to the reaction mixture, followed by phase separation. The aqueous phase was removed to obtain the organic phase. The organic phase thus obtained was subjected to distillation at a reduced pressure to obtain (3Z, 13Z)-3,13-octadecadienyl acetate (7) (116.35 g, 0.36 mol, purity 95.03, b.p.=136.9 to 145.1° C./0.40 kPa (3.0 mmHg)) in a yield of 100%.

The following are spectrum data of the (3Z,13Z)-3,13-octadecadienyl acetate (7) thus prepared.

Nuclear magnetic resonance spectrum: 1H-NMR (500 MHZ, CDCl$_3$): δ=0.89 (3H, t, J=7.3 Hz), 1.24-1.38 (16H, m), 1.98-2.06 (6H, m), 2.04 (3H, s), 2.37 (2H, q-like, J=7.1 Hz), 4.05 (2H, t, J=6.9 Hz), 5.30-5.38 (3H, m), 5.50 (1H, dtt, J=10.7 Hz, 7.3 Hz, 1.5 Hz); $^{13}$C-NMR (500 MHz, CDCl$_3$): δ=13.96, 20.94, 22.32, 26.79, 26.89, 27.16, 27.28, 29.25, 29.47, 29.49, 29.57, 29.73, 31.94, 63.96, 124.21, 129.83, 132.97, 171.08. Mass spectrum: EI-mass spectrum (70 eV): m/z 308 (M$^+$), 248, 219, 191, 163, 135, 109, 81, 65, 43.

Infrared absorption spectrum (D-ATR): νmax=2926, 2854, 1745, 1465, 1383, 1363, 1237, 1036, 723.

Example 10: Preparation of (3Z,13E)-3,13-octadiene methoxymethyl ether (5: $R^1$=H)

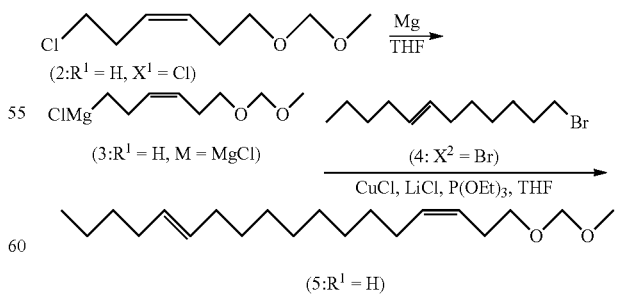

Magnesium (5.07 g, 0.21 grams atom) and tetrahydrofuran (59.78 g) were placed in a reactor at room temperature and stirred at 60 to 65° C. for 16 minutes. After the completion of the stirring, the (3Z)-6-chloro-3-hexenyl methoxymethyl ether (2: $R^1$=H, $X^1$=Cl) (36.58 g, 0.20 mol, purity 97.33%) obtained in Example 6 was added dropwise at 60 to 75° C. After the completion of the dropwise addition, the reaction mixture was stirred at 75 to 80° C. for 2 hours to prepare (3Z)-6-(methoxymethoxy)-3-hexenylmagnesium chloride (3: $R^1$=H, M=MgCl).

Subsequently, cuprous chloride (0.21 g, 0.0021 mol), lithium chloride (0.15 g, 0.0035 mol), triethyl phosphite (2.13 g, 0.013 mol), tetrahydrofuran (37.96 g), and (5E)-12-bromo-5-dodecene (4: $X^2$=Br) (47.23 g, 0.19 mol, purity 99.37%) were placed in another reactor, and the (3Z)-6-(methoxymethoxy)-3-hexenylmagnesium chloride (3: $R^1$=H, M=MgCl) prepared above was added dropwise at 15 to 30° C. After the completion of the dropwise addition, the reaction mixture was stirred at 15 to 25° C. for 3 hours. After the completion of the stirring, an aqueous solution of ammonium chloride (2.09 g) in water (54.28 g) and hydrochloric acid (3.99 g, 0.022 mol of hydrogen chloride) were added sequentially to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z,13E)-3,13-octadiene methoxymethyl ether (5: $R^1$=H) (59.78 g, 0.18 mol, purity 92.42%, b.p.=130.0 to 145.9° C./0.40 kPa (3.0 mmHg)) in a yield of 93.75%.

The following are spectrum data of the (3Z,13E)-3,13-octadiene methoxymethyl ether (5: $R^1$=H) thus prepared.

Nuclear magnetic resonance spectrum: 1H-NMR (500 MHZ, CDCl$_3$): δ=0.88 (3H, t, J=7.3 Hz), 1.23-1.38 (16H, m), 1.93-2.00 (4H, m), 2.04 (2H, dt, J=7.3 Hz, 7.3 Hz), 2.34 (2H, q-like, J=6.9 Hz), 3.36 (3H, s), 3.53 (2H, t, J=6.9 Hz), 4.62 (2H, s), 5.32-5.43 (3H, m), 5.47 (1H, dtt, J=10.7 Hz, 7.3 Hz, 1.6 Hz); $^{13}$C-NMR (500 MHZ, CDCl$_3$): δ=13.94, 22.17, 27.33, 27.88, 29.14, 29.27, 29.46, 29.49, 29.59, 29.63, 31.82, 32.27, 32.58, 55.10, 67.40, 96.32, 125.33, 130.29, 130.31, 132.20.

Mass spectrum: EI-mass spectrum (70 eV): m/z 310 (M$^+$), 278, 248, 221, 151, 135, 109, 81, 45, 29.

Infrared absorption spectrum (D-ATR): vmax=2925, 2854, 1465, 1151, 1111, 1037, 967, 920, 724.

Example 11: Preparation of (3Z,13E)-3,13-octadecadien-1-ol (6)

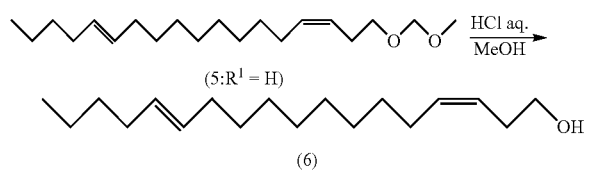

The (3Z,13E)-3,13-octadiene methoxymethyl ether (5: $R^1$=H) (59.54 g, 0.18 mol, purity 92.42%) obtained in Example 10, methanol (88.60 g, 2.77 mol), and 20% hydrochloric acid (8.86 g, 0.045 mol of hydrogen chloride) were placed in a reactor equipped with a distillation tower, and the reaction mixture was heated to 60° C. and stirred for 1 hour. After the completion of the stirring, the internal temperature was raised to 65 to 70° ° C. to distill off a mixture of by-produced dimethoxymethane and methanol from the distillation tower. The reaction mixture was sampled during the reaction. After the conversion was confirmed to be 100%, water (53.16 g) was added to the reaction mixture, followed by phase separation. The aqueous phase was removed to obtain the organic phase. The organic phase thus obtained was subjected to distillation at a reduced pressure to obtain (3Z,13E)-3,13-octadecadien-1-ol (6) (47.35 g, 0.16 mol, purity 91.11%, b.p.=131.2 to 150.0° C./0.40 kPa (3.0 mmHg)) in a yield of 91.34%.

The following are spectrum data of the (3Z,13E)-3,13-octadecadien-1-ol (6) thus prepared.

Nuclear magnetic resonance spectrum: 1H-NMR (500 MHZ, CDCl$_3$): δ=0.88 (3H, t, J=7.3 Hz), 1.22-1.38 (16H, m), 1.54 (1H, br. s), 1.93-2.00 (4H, m), 2.05 (2H, q-like, J=6.9 Hz), 2.32 (2H, q-like, J=6.9 Hz), 3.63 (2H, t, J=6.5 Hz), 5.32-5.42 (3H, m), 5.55 (1H, dtt, J=11.1 Hz, 7.3 Hz, 1.6 Hz); $^{13}$C-NMR (500 MHZ, CDCl$_3$): δ=13.93, 22.16, 27.34, 29.12, 29.27, 29.44, 29.47, 29.61, 29.67, 30.76, 31.81, 32.26, 32.57, 62.30, 124.89, 130.29, 133.52.

Mass spectrum: EI-mass spectrum (70 eV): m/z 266 (M$^+$), 248, 222, 208, 194, 177, 163, 149, 135, 121, 109, 95, 81, 55, 41.

Infrared absorption spectrum (D-ATR): vmax=3330, 2924, 2854, 1465, 1049, 967, 723.

Example 12: Preparation of (3Z,13E)-3,13-octadecadienyl acetate (7)

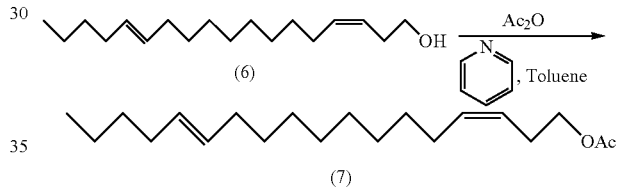

The (3Z,13E)-3,13-octadecadien-1-ol (6) (44.25 g, 0.15 mol, purity 91.11%) obtained in Example 11, toluene (33.16 g), and pyridine (22.74 g, 0.29 mol) were placed in a reactor at room temperature and stirred at 15 to 25° C. for 2 minutes. After the completion of the stirring, acetic anhydride (23.17 g, 0.23 mol) was added dropwise at 20 to 40° C. and stirred at 30 to 35° C. for 7 hours. Next, water (39.74 g) was added to the reaction mixture, followed by phase separation. The aqueous phase was removed to obtain the organic phase. The organic phase thus obtained was subjected to distillation at a reduced pressure to obtain (3Z,13E)-3,13-octadecadienyl acetate (7) (46.68 g, 0.15 mol, purity 95.68, b.p.=133.9 to 141.2° C./0.40 kPa (3.0 mmHg)) in a yield of 100%.

The following are spectrum data of the (3Z,13E)-3,13-octadecadienyl acetate (7) thus prepared.

Nuclear magnetic resonance spectrum: 1H-NMR (500 MHz, CDCl$_3$): δ=0.88 (3H, t, J=7.3 Hz), 1.22-1.38 (16H, m), 1.93-1.99 (4H, m), 2.03 (2H, q-like, J=6.9 Hz), 2.04 (3H, s), 2.37 (2H, q-like, J=7.1 Hz), 4.05 (2H, t, J=6.9 Hz), 5.33 (1H, dtt, J=11.1 Hz, 7.3 Hz, 1.5 Hz), 5.36-5.40 (2H, m), 5.50 (1H, dtt, J=10.7 Hz, 7.3 Hz, 1.5 Hz); 13C-NMR (500 MHz, CDCl$_3$): δ=13.93, 20.95, 22.16, 26.78, 27.29, 29.13, 29.25, 29.44, 29.49, 29.58, 29.62, 31.81, 32.26, 32.58, 63.96, 124.20, 130.30, 132.98, 171.08.

Mass spectrum: EI-mass spectrum (70 eV): m/z 308 (M$^+$), 248, 219, 191, 163, 135, 109, 81, 65, 43.

Infrared absorption spectrum (D-ATR): vmax=2925, 2854, 1745, 1465, 1363, 1237, 1036, 967, 724.

The invention claimed is:

1. A 6-hydroxy-3-hexenyl alkoxymethyl ether compound of the following general formula (1):

$$HOCH_2CH_2CH=CHCH_2CH_2OCH_2OCH_2R^1 \quad (1)$$

wherein $R^1$ represents a hydrogen atom, an n-alkyl group having 1 to 9 carbon atoms, or a phenyl group.

* * * * *

UNITED STATES PATENT AND TRADEMARK OFFICE
CERTIFICATE OF CORRECTION

PATENT NO. : 12,060,323 B2
APPLICATION NO. : 18/303008
DATED : August 13, 2024
INVENTOR(S) : Miyake et al.

It is certified that error appears in the above-identified patent and that said Letters Patent is hereby corrected as shown below:

On the Title Page

(57) Abstract: Please correct "$CH_3(CH_2)_3CH—CH(CH_2)_8CH=CHCH_2CH_2OH$" to read --$CH_3(CH_2)_3CH=CH(CH_2)_8CH=CHCH_2CH_2OH$--

In the Specification

Column 5, Line 5: Please correct "$R^1CH_2OCH_2OCH_2CH_2CHECHCH_2CH_2OH$" to read --$R^1CH_2OCH_2OCH_2CH_2CH=CHCH_2CH_2OH$--

Column 24, Line 35: Please correct "65° ° C." to read --65 °C.--

Column 26, Line 6: Please correct "1H-NMR" to read --$^1$H-NMR--

Column 26, Line 7: Please correct "MHZ" to read --MHz--

Column 26, Line 54: Please correct "1H-NMR" to read --$^1$H-NMR--

Column 27, Line 10: Please correct "(9:$R^1$=PH)" to read --(9:$R^1$=Ph)--

Column 27, Line 32: Please correct "1H-NMR" to read --$^1$H-NMR--

Column 28, Line 18: Please correct "1H-NMR" to read --$^1$H-NMR--

Column 28, Line 23: Please correct "MHZ" to read --MHz--

Column 29, Line 12: Please correct "1H-NMR" to read --$^1$H-NMR--

Column 29, Line 13: Please correct "MHZ" to read --MHz--

Signed and Sealed this
Third Day of June, 2025

Coke Morgan Stewart
*Acting Director of the United States Patent and Trademark Office*

Column 29, Line 17: Please correct "MHZ" to read --MHz--

Column 29, Line 58: Please correct "1H-NMR" to read --$^1$H-NMR--

Column 29, Line 59: Please correct "MHZ" to read --MHz--

Column 29, Line 62: Please correct "MHZ" to read --MHz--

Column 30, Line 24: Please correct "35° ° C." to read --35 °C.--

Column 30, Line 34: Please correct "1H-NMR" to read --$^1$H-NMR--

Column 30, Line 35: Please correct "MHZ" to read --MHz--

Column 30, Line 41: Please insert a paragraph break between "171.08." and "Mass"

Column 31, Line 30: Please correct "1H-NMR" to read --$^1$H-NMR--

Column 31, Line 31: Please correct "MHZ" to read --MHz--

Column 31, Line 35: Please correct "MHZ" to read --MHz--

Column 31, Line 64: Please correct "70° ° C." to read --70 °C.--

Column 32, Line 10: Please correct "1H-NMR" to read --$^1$H-NMR--

Column 32, Line 11: Please correct "MHZ" to read --MHz--

Column 32, Line 15: Please correct "MHZ" to read --MHz--

Column 32, Line 54: Please correct "1H-NMR" to read --$^1$H-NMR--

Column 32, Line 59: Please correct "13C-NMR" to read --$^{13}$C-NMR--